US009993199B2

(12) United States Patent
Berzowska et al.

(10) Patent No.: US 9,993,199 B2
(45) Date of Patent: Jun. 12, 2018

(54) TEXTILE BLANK WITH SEAMLESS KNITTED ELECTRODE SYSTEM

(71) Applicant: OMsignal Inc., Montreal (CA)

(72) Inventors: Joanna Berzowska, Montreal (CA); Frederic Chanay, Montreal (CA); Stephane Menard, St-Bruno (CA); Elina Nurkka, Verdun (CA)

(73) Assignee: OMsignal Inc., Montreal, QC (CA)

( * ) Notice: Subject to any disclaimer, the term of this patent is extended or adjusted under 35 U.S.C. 154(b) by 990 days.

(21) Appl. No.: 14/249,011

(22) Filed: Apr. 9, 2014

(65) Prior Publication Data

US 2014/0343390 A1 Nov. 20, 2014

Related U.S. Application Data

(60) Provisional application No. 61/810,313, filed on Apr. 10, 2013.

(51) Int. Cl.
*A61B 5/04* (2006.01)
*A61B 5/00* (2006.01)
(Continued)

(52) U.S. Cl.
CPC .............. *A61B 5/6804* (2013.01); *A61B 5/01* (2013.01); *A61B 5/02055* (2013.01);
(Continued)

(58) Field of Classification Search
CPC ... A61B 5/6804; A61B 5/6805; A61B 5/6806; A61B 5/6807; A61B 5/6802;
(Continued)

(56) References Cited

U.S. PATENT DOCUMENTS 4,722,354 A † 2/1988 Axelgaard
5,374,283 A † 12/1994 Flick
(Continued)

FOREIGN PATENT DOCUMENTS

EP 1858581 A2 11/2007
WO 2006101748 A2 9/2006
(Continued)

OTHER PUBLICATIONS

International Preliminary Report on Patentability, dated Oct. 13, 2015 for PCT/CA2014/050366, filed Apr. 9, 2014.
(Continued)

*Primary Examiner* — Lee S Cohen
*Assistant Examiner* — Eunhwa Kim
(74) *Attorney, Agent, or Firm* — Cooley LLP

(57) ABSTRACT

A textile-based electrode system includes a first fabric layer having an inner and an outer surface. The inner surface includes a knitted electrode configured to be placed in contact with the skin of a user. A second fabric layer is disposed and configured to contact the outer surface of the first fabric layer. The second fabric layer includes a knitted conductive pathway configured to be electrically coupled to the knitted electrode. Furthermore, a third fabric layer is configured and disposed to contact the second fabric layer. A connector is disposed on the third fabric layer and is configured to be electrically coupled to the knitted conductive pathway. The second fabric layer can be folded about a first fold axis and the third fabric layer can be folded about a second fold axis to place the second fabric layer in contact with the first fabric layer and the third fabric layer.

20 Claims, 24 Drawing Sheets

(51) Int. Cl.

| | | |
|---|---|---|
| *A61B 5/0408* | (2006.01) | |
| *A61B 5/01* | (2006.01) | |
| *A61B 5/0205* | (2006.01) | |
| *A61B 5/0492* | (2006.01) | |
| *A61B 5/113* | (2006.01) | |
| *D04B 1/14* | (2006.01) | |
| *D04B 1/22* | (2006.01) | |
| *H05K 1/03* | (2006.01) | |
| *H05K 1/11* | (2006.01) | |
| *H05K 3/30* | (2006.01) | |
| *D04B 1/24* | (2006.01) | |
| *A61B 5/0245* | (2006.01) | |
| *A61B 5/053* | (2006.01) | |
| *A61B 5/08* | (2006.01) | |
| *A61B 5/091* | (2006.01) | |
| *A41D 13/12* | (2006.01) | |

(52) U.S. Cl.
CPC .......... *A61B 5/0408* (2013.01); *A61B 5/0492* (2013.01); *A61B 5/1135* (2013.01); *D04B 1/14* (2013.01); *D04B 1/225* (2013.01); *D04B 1/24* (2013.01); *H05K 1/038* (2013.01); *H05K 1/11* (2013.01); *H05K 3/30* (2013.01); *A41D 13/1281* (2013.01); *A61B 5/0245* (2013.01); *A61B 5/0533* (2013.01); *A61B 5/0816* (2013.01); *A61B 5/091* (2013.01); *A61B 2562/125* (2013.01); *D10B 2403/02431* (2013.01); *D10B 2509/00* (2013.01); *Y10T 29/49147* (2015.01)

(58) Field of Classification Search
CPC ... A61B 5/6803; A61B 5/0408; A61B 5/0492; A61B 5/053; A41D 13/1281; H05K 1/11; H05K 1/038; H05K 3/30; D04B 1/24; D04B 1/225; D04B 1/14; D10B 2403/02431; D10B 2509/00
USPC .................................................. 600/388, 389
See application file for complete search history.

(56) References Cited

U.S. PATENT DOCUMENTS

| | | | |
|---|---|---|---|
| 5,450,845 | A † | 9/1995 | Axelgaard |
| 6,381,482 | B1 † | 4/2002 | Jayaraman |
| 6,970,731 | B1 † | 11/2005 | Jayaraman |
| 7,970,451 | B2 † | 6/2011 | Hassonjee |
| 8,082,762 | B2 † | 12/2011 | Burr |
| 2008/0143080 | A1 | 6/2008 | Burr |
| 2009/0270708 | A1* | 10/2009 | Shen .................. A61B 5/02438 600/389 |
| 2010/0070007 | A1 | 3/2010 | Parker et al. |

FOREIGN PATENT DOCUMENTS

| | | |
|---|---|---|
| WO | 2009013704 A2 | 1/2009 |
| WO | 2012066056 A1 | 5/2012 |

OTHER PUBLICATIONS

International Search Report dated Jul. 21, 2014 for PCT/CA2014/050366, filed Apr. 9, 2014.

\* cited by examiner
† cited by third party

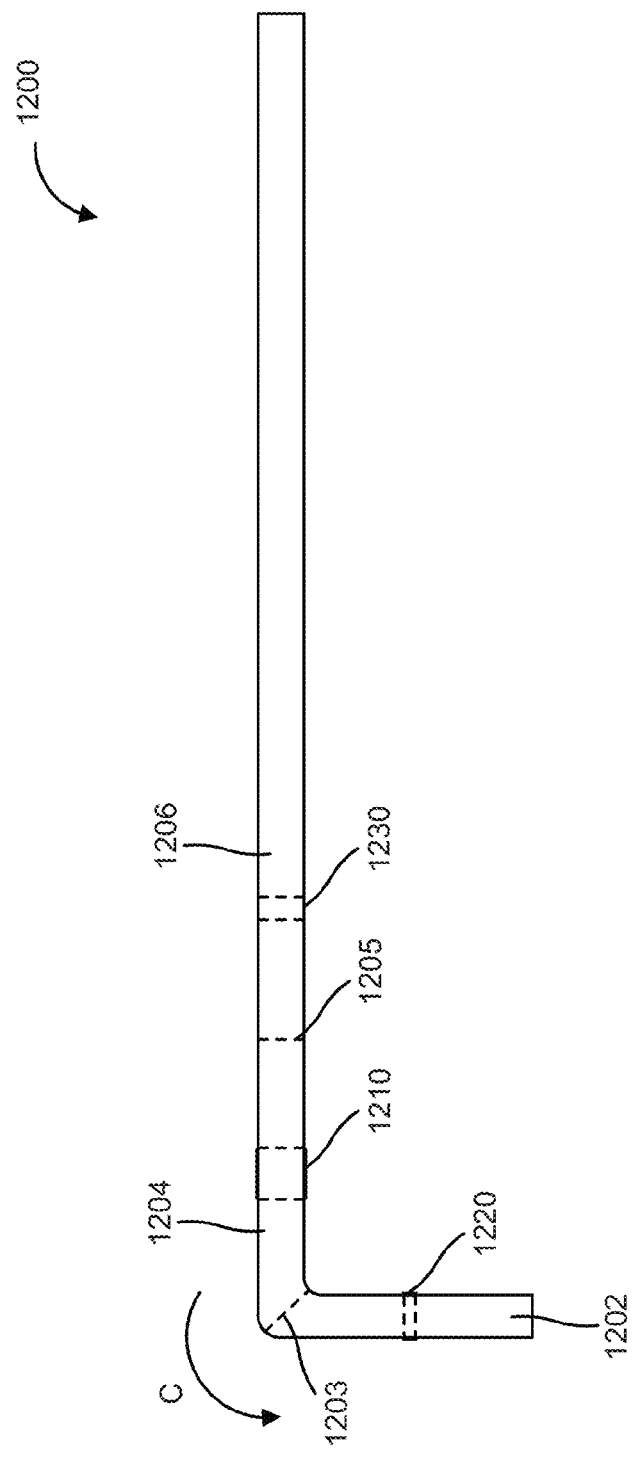

TEXTILE BLANK WITH SEAMLESS KNITTED ELECTRODE SYSTEM

CROSS REFERENCE TO RELATED APPLICATIONS

This application claims priority to and the benefit of U.S. Provisional Patent Application No. 61/810,313, entitled "Textile Blank with Seamless Knitted Electrode System," filed Apr. 10, 2013, the disclosure of which is incorporated herein by reference in its entirety.

BACKGROUND

Embodiments described herein relate generally to wearable systems, devices and methods for measuring physiological parameters, and in particular to textile-based electrode systems that include sensors for measuring various physiological parameters.

Real time monitoring of physiological parameters over extended periods of time poses significant challenges. Conventional instruments and devices for sensing physiological parameters such as, for example, galvanic skin response (GSR), heart rate, breathing rate, etc. can include electrodes that are coupled to a user via leads. Such devices can cause discomfort to the user and/or restrict the user's movements, which can make it relatively challenging to measure the physiological parameters of the user in real time.

Textile-based electrode systems that include electrodes integrated, printed, laminated, stitched, knitted, or sewn within the system or garment can overcome the challenges of real-time physiological monitoring. Such systems can be worn by the user such that the electrodes included in the wearable textile are in contact with the skin of the user and can thereby measure one or more physiological parameters of the user.

State of the art wearable textile-based electrode systems suffer from numerous shortcomings. Some conventional textile-based electrode systems include electrodes that are stitched or sewn into the system. Stitched or sewn electrodes can rub against the user's skin causing chafing or rashes, which can cause discomfort to the user. Furthermore, stitched or sewn electrodes are prone to wear and tear, for example, because of repeated use or washing. This can reduce the life of the system. Moreover, stitched or sewn electrodes can increase the overall cost of the system.

Other conventional textile-based electrode systems are configured to work with only two electrodes. In such systems, the electrodes generally need to be located and aligned proximate to each other to allow an electrical device (e.g., a sensor or a processing module) to be coupled to the electrodes such that the electrical device is located between the electrodes.

Thus, there is a need for improved textile-based electrode systems that minimally impact the comfort of the user, have long life, and provide greater signal quality and accuracy.

SUMMARY

Embodiments described herein relate generally to wearable systems, devices and methods for measuring physiological parameters, and in particular to textile-based electrode systems that include sensors for measuring various physiological parameters. In some embodiments, a textile-based electrode system includes a first fabric layer having an inner surface and an outer surface. The inner surface includes a knitted electrode configured to be placed in contact with the skin of a user. A second fabric layer is disposed and configured to contact the outer surface of the first fabric layer. The second fabric layer includes a knitted conductive pathway configured to be electrically coupled to the knitted electrode. Furthermore, a third fabric layer is configured and disposed to contact the second fabric layer. A connector is disposed on the third fabric layer and is configured to be electrically coupled to the knitted conductive pathway. In some embodiments, the second fabric layer is folded about a first fold axis to place the second fabric layer in contact with the outer surface of the first fabric layer. In some embodiments, the third fabric layer is folded about a second fold axis to place the third fabric layer in contact with the second fabric layer.

BRIEF DESCRIPTION OF THE DRAWINGS

FIG. 5B shows a side view of the system with a first fabric portion of the system partially folded along a first fold line.

DETAILED DESCRIPTION

Figure 1:
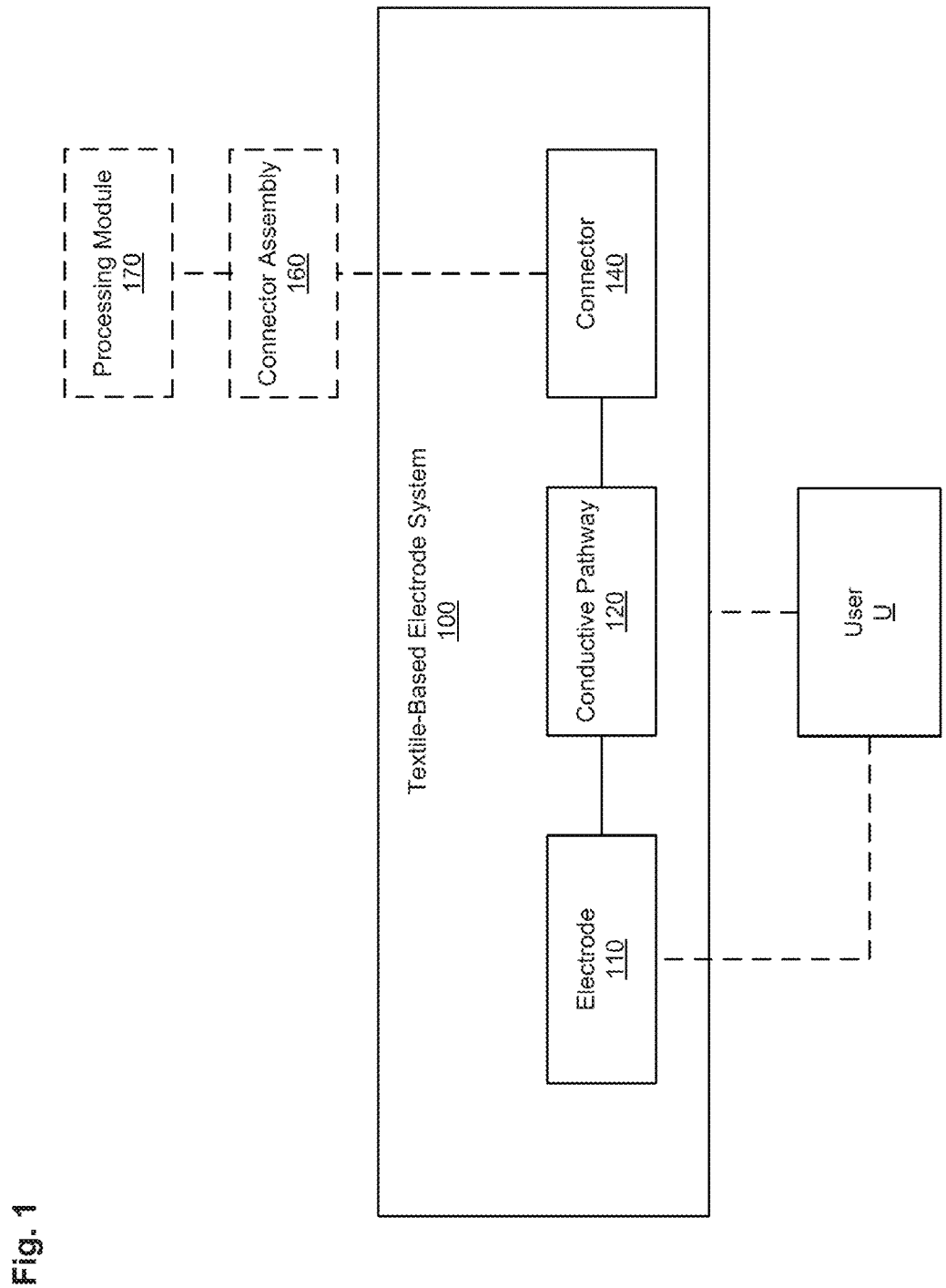
FIG. 1 is a schematic illustration of a textile-based electrode system, according to an embodiment.

Embodiments described herein relate generally to wearable systems, devices and methods for measuring physiological parameters, and in particular to textile-based electrode systems that include sensors for measuring various physiological parameters. Some conventional textile-based electrode systems include electrodes that are stitched or sewn into the textile, which can cause discomfort to a user, for example, by causing chafing or rashes on the skin of the user. Furthermore, stitched or sewn electrodes are prone to wear and tear, for example, because of repeated use or washing, which can reduce the life of the system. Moreover, stitched or sewn electrodes can increase the overall cost of the system.

Embodiments of a textile-based electrode system described herein provide several advantages over known textile-based electrode systems such as, for example: (1) providing knitted electrodes and knitted conductive pathways such that no stitching or sewing is required; (2) seamlessly knitting the electrodes and conductive pathways within the fabric of the textile-based electrode systems such that the systems are more economical, efficient and scalable for mass production; (3) providing a plurality of electrodes configured to sense multiple physiological parameters; (4) providing higher comfort level to a user wearing the system by reducing chafing and pressure on skin that can be caused by seams or stitches; and (5) having longer life. Embodiments of the textile based electrode system described herein can be included in a wearable textile, for example, a waist band, a vest, a bra, a shirt, a jersey, an arm band, a thigh band, an ankle band, a belt, a head band, a chest plate, any other wearable textile or a combination thereof.

In some embodiments, a textile-based electrode system includes a first fabric layer having an inner surface and an outer surface. The inner surface includes a knitted electrode configured to be placed in contact with the skin of a user. A second fabric layer is disposed and configured to contact the outer surface of the first fabric layer. The second fabric layer includes a knitted conductive pathway configured to be electrically coupled to the knitted electrode. A third fabric layer is configured and disposed to contact the second fabric layer. A connector is disposed on the third fabric layer and is configured to be electrically coupled to the knitted conductive pathway. In some embodiments, the second fabric layer is folded about a first fold axis to place the second fabric layer in contact with the outer surface of the first fabric layer. In some embodiments, the third fabric layer is folded about a second fold axis to place the third fabric layer in contact with the second fabric layer.

In some embodiments, a textile-based electrode system can include a first fabric portion which includes a knitted conductive pathway. A second fabric portion is coupled to the first fabric portion and includes a knitted electrode configured to be placed in contact with the skin of a user. The second fabric portion is folded over the first fabric portion along a first fold line such that the knitted electrode is configured to be electrically coupled to the knitted conductive pathway. A third fabric portion is coupled to the second fabric portion and includes a connector region. The third fabric portion is folded over the first fabric portion along a second fold line such that (a) the connector region is configured to be coupled to the knitted conductive pathway, and (b) the first fabric portion is disposed between the second fabric portion and the third fabric portion. In some embodiments, the first fabric portion, the second fabric portion, and the third fabric portion are substantially tubular. In some embodiments, the first fabric portion, the second fabric portion, and the third fabric portion are formed seamlessly.

In some embodiments, a method for manufacturing a textile-based electrode system includes knitting a first tubular portion including a conductive pathway. A second tubular portion which includes an electrode is knitted extending from the first tubular portion. A third tubular portion is knitted extending from the second tubular portion. The first tubular portion is folded over the second tubular portion along a first fold line and the conductive pathway is electrically coupled to the electrode. The first tubular portion and the second tubular portion are then folded over the third tubular portion along a second fold line such that the first tubular portion is disposed between the second tubular portion and the third tubular portion. A connector is disposed in the third fabric portion. The conductive pathway is then coupled to the connector. In some embodiments, the method further includes coupling the first tubular portion to the second tubular portion after the first fold. In some embodiments, the method also includes coupling the third tubular portion to the second tubular portion and the first tubular portion adjacent the first fold line such that the first tubular portion and the second tubular portion remain folded over the third tubular portion during use.

As used herein, the term "about" and "approximately" generally mean plus or minus 10% of the value stated, for example about 250 μm would include 225 μm to 275 μm, about 1,000 μm would include 900 μm to 1,100 μm.

As used herein, the terms "continuously," "seamless" and "seamlessly" refer to the integration of layers, portions, or components included in a textile-based electrode system without any seams, interruptions, transitions, or indications of disparity resulting in a visually appealing appearance which improves a user comfort by reducing chafing and pressure on the skin that are usually caused by seams.

As used herein, the term "knit" or "knitted" refers to layers, portions, or components included in a textile-based electrode system that are formed by interlacing yarn or threads in a series of connected loops with needles.

As used herein, the term "electrode" refers to an electrical conductor configured to contact a non-metallic surface including a skin of a user (e.g., a human or an animal) and measure electrical signals corresponding to one or more physiological parameters of the user.

FIG. 1 shows a schematic illustration of a textile-based electrode system 100, according to an embodiment. The system 100 includes an electrode 110, a conductive pathway 120, and a connector 140. Optionally, a connector assembly 160 can be coupled to the connector 140 and configured to electrically couple the connector 140 to a processing module 170. The system 100 is configured to be associated with a user U, for example, worn by the user U such that the electrode 110 is in contact with the skin of the user.

In some embodiment, the system 100 can include a first fabric layer that has an inner surface and an outer surface. The inner surface can include the electrode 110 and can be configured to be placed in contact with the skin of the user U such that the electrode 110 also contacts the skin of the user U. The electrode 110 can be continuously and seamlessly knitted into the first layer. The electrode 110 can be knitted from a conductive yarn such as, for example, XSTATIC® silver metalized yarn, stainless steel thread, SCHOELLER® wool, polyaniline yarn, any other suitable conductive yarn or combination thereof. The electrode 110 can have any suitable size or shape such as, for example, square, rectangular, circular, elliptical, oval, polygonal, or any other suitable shape. While shown as including a single electrode 110, in some embodiments, the system 100 can include a plurality of electrodes 110, for example, 2, 3, 4, 5, or even more. In some embodiments, a padding member can be disposed on the outer surface of the first fabric layer adjacent to the electrodes. The padding member can be formed from any suitable material such as, for example, rubbery foam, a sponge, memory foam, a 3-D knitted porous fabric (e.g., a 3-D knitted mesh or 3-D spacer knit), any other suitable material or combination thereof. The padding member can, for example, be configured to urge the electrode 110 towards the skin of the user U, for example, to enable efficient contact of the electrode 110 with the skin of the user U. In some embodiments, the padding member can be also be configured to prevent rubbing of the electrode 110 against a fabric layer adjacent to the electrode, for example, a second fabric layer as described herein, and reduce noise. The electrode 110 can be configured to contact a skin of the user U and measure an electrical signal corresponding to a physiological parameter of the user U. The physiological parameters that can be measured include but are not limited to a galvanic skin response (GSR), an electrocardiogram (ECG), a heart rate, a breathing rate, a breathing pattern, a rib cage perimeter, a rib cage volume, an electromyelogram, and a body temperature.

In some embodiments, the system 100 can include a second fabric layer that includes the conductive pathway 120. In such embodiments, the conductive pathway 120 can be continuously and seamlessly knitted into the second fabric layer. The second fabric layer can be disposed and configured to contact the outer surface of the first fabric layer such that the conductive pathway 120 can be electrically coupled to the electrode 110. The conductive pathway 120 can be knitted from a conductive yarn such as, for example, XSTATIC® silver metalized yarn, stainless steel thread, SCHOELLER® wool, polyaniline yarn, any other suitable conductive yarn or combination thereof. While shown as including a conductive pathway 120, in some embodiments, the system 100 can include a plurality of conductive pathways 120, for example, 2, 3, 4, 5, or even more, corresponding to the number of electrodes 110 included in the system 100. The conductive pathway 120 is configured to electrically couple the electrode 110 to the connector 140 disposed on a third fabric layer, as described herein. In some embodiments, the connector 140 can disposed on the second fabric layer and electrically coupled to the conductive pathway 120. In some embodiments, the conductive pathway 120 can be coupled to the electrode 110 using conductive yarn. In some embodiments, the conductive pathway 120 can be coupled to the electrode 110 with stitching, sewing, an adhesive (e.g., with conductive glue or conductive epoxy), a hot wire press, high frequency welding, ultrasonic welding, or any other suitable coupling mechanism.

In some embodiments, an insulating member can be disposed on the conductive pathway 120, for example, by over printing or laminating the conductive pathway 120 with any suitable insulating material such as, for example, a heat sealed adhesive, insulating membrane, polymers, plastics, mica, fabric, etc. In some embodiments, the insulating member can be configured to electrically isolate the conductive pathway 120 from the first fabric layer and/or the third fabric layer, for example, to reduce signal noise caused by rubbing of the conductive pathway against the first and/or the third fabric layer and thereby, improve signal quality. In some embodiments, the insulating member can be configured to provide a moisture impervious barrier, for example, to prevent electrical shorts.

In some embodiments, the system 100 can include a third fabric layer configured and disposed to contact the second fabric layer. The connector 140 can be disposed on the third fabric layer and configured to be electrically coupled to the knitted conductive pathway 120. In some embodiments, the third fabric portion can include an opening. The connector 140 can be at least partially disposed in the opening such that the connector 140 can be coupled to the knitted conductive pathway 120. The third fabric layer can be disposed and configured to contact the second fabric layer such that the connector 140 can be electrically coupled to the conductive pathway 120 using any suitable means, as described herein, for example, mechanical coupling. In some embodiments, the third fabric layer can include one or more connector regions (not shown) configured to be electrically coupled to the knitted conductive pathway 120. The connector regions can be knitted from a conductive yarn such as, for example, XSTATIC® silver metalized yarn, stainless steel thread, SCHOELLER® wool, polyaniline yarn, any other suitable conductive yarn or combination thereof. While shown as including a single connector 140, in some embodiments, the system 100 can include a plurality of connectors 140, for example, 2, 3, 4, 5, or even more, for example, corresponding to the number of electrodes 110 included in the system 100. The connector 140 can be configure to be electrically coupled to the conductive pathway 120 using mechanical coupling, an adhesive (e.g., with a conductive adhesive or epoxy), a hot wire press, high frequency welding, ultrasonic welding, sewing or stitching with conductive yarn, any other suitable coupling mechanism or combination thereof. The connector 140 can include a snap-fit connector (e.g., a male or female connector, a pin socket connector, a DIN connector, a banana connector, etc.), a hook connector, a magnetic connector, any other suitable connector or a combination thereof. In some embodiments, at least a portion of the connector 140, for example, a portion coupled to the conductive pathway 120 can be laminated or otherwise insulated with a suitable insulating material such as, for example, a heat sealed adhesive, polymers, plastics, mica, fabric, etc. The connector 140 can be configured to be removably coupled to a connector assembly 160 such that the connector region 140 is in electrical communication with the connector assembly 160.

The connector assembly 160 can include one or more connector receivers configured to mate with the connectors 140. The connector receivers can be disposed and coupled to an electric circuit, for example, a printed electric circuit that can be disposed on a substrate, for example, a flat substrate. The connector assembly 160 can be ergonomically designed, have a small size, and light weight such that connector assembly 160 can be disposed on the system 100 (e.g., on the third fabric layer) while in use by the user U. In some embodiments, the third fabric layer can include a cover layer (e.g., a pocket) configured to cover at least a portion of the connector assembly 160, such that the connector assembly 160 is hidden from sight.

The connector assembly 160 can be in electrical communication with the processing module 170 and configured to convey the electrical signals from the electrode 110 to the processing module 170. The processing module 170 can be configured to analyze the electrical signals received from the electrodes 110 and correlate the signals to one or more physiological parameters of the user U. In some embodiments, the processing module 170 can include a transimpedance amplifier circuit configured to convert current to an amplified voltage. In some embodiments, the processing module 170 can include an analog to digital converter configured to digitize the voltage. For example, the processing module 170 can include a differential analog to digital converter which can reduce noise in the signal measurement. In some embodiments, the processing module 170 can include operational amplifiers configured to amplify the measured signal. In some embodiments, the processing module 170 can include a filtering circuit, for example, a low pass filter, a high pass filter, a band pass filter, any other suitable filtering circuit, or combination thereof, configured to substantially reduce signal noise.

In some embodiments, the processing module 170 can include a processor, for example, a microcontroller, a microprocessor, an ASIC chip, an ARM chip, or a programmable logic controller (PLC). The processor can include signal processing algorithms, for example, band pass filters, low pass filters, any other signal processing algorithms or combination thereof. In some embodiments, the processing module 170 can include a memory configured to store at least one of an electrical signal data, algorithms, user log data, etc. In some embodiments, the memory can also be configured to store a reference signature, for example, a calibration equation.

The first fabric layer, the second fabric layer, and the third fabric layer can be knit from a non-conducting yarn such as, for example, nylon, cotton, silk, ramie, polyester, latex, spandex, any other suitable non-conductive yarn or combination thereof. The knitting can be performed using an SM8-TOP2 knitting machine by SANTONI™ or any other suitable knitting machine. Any suitable knitting pattern can be used, for example, single, double, jersey, interlocked, mock rib, ribbed, two-way stretch fabric, any other suitable knitting pattern or combination thereof. In some embodiments, the knitting pattern can intermesh on both sides of the fabric layer. In some embodiments, the knitted fabric layers can include a float yarn. In some embodiments, the first fabric layer can be continuously formed with the second fabric layer (e.g., seamlessly knitted). In some embodiments, the first fabric layer can also be continuously formed with the third fabric layer (e.g., seamlessly knitted). In some embodiment, the second fabric layer can be folded about a first fold axis to place the second fabric layer in contact with the outer surface of the first fabric layer such that, for example, the conductive pathway 120 can be electrically coupled to the electrode 110. Furthermore, the third fabric layer can be folded about a second fold axis to place the third fabric layer in contact with the second fabric layer such that, for example, the conductive pathway 120 can be coupled to the connector 140. In such embodiments, the first fabric layer can be coupled to the second fabric layer and the third fabric layer along at least one of the first fold axis and the second fold axis using any suitable coupling means such as, for example, stitching, sewing, gluing, hot wire press, high frequency welding, ultrasonic welding, any other suitable coupling mechanism or combination thereof. Any of the non-conductive yarn used for knitting the fabric layers, and the conductive-yarn used for knitting the electrode 110, and the conductive pathways 120 can be inelastic or elastic. For example, elastic conductive yarn and elastic non-conductive yarn can be used to form a textile-based electrode system included in a sports garment or textile.

In some embodiments, the system 100 can include a first fabric portion that includes the knitted conductive pathway 120. The system 100 can include a second fabric portion coupled to the first fabric portion (e.g., continuously formed or seamlessly coupled). The second fabric portion can include the knitted electrode 110 configured to be placed in contact with the user. The second fabric portion can be folded along a first fold line such that the knitted electrode 110 is configured to be electrically coupled to the knitted conductive pathway 120, for example, using conductive yarn or any other coupling mechanism described herein. The system 100 can also include a third fabric portion including a connector region and coupled to the second fabric portion (e.g., continuously formed or seamlessly coupled). The third fabric portion can be folded over the first fabric portion along a second fold line such that (a) the connector region is configured to be coupled to the knitted conductive pathway 120 by the connector 140 (e.g., by electrically and/or mechanically coupling the connector 140 to the knitted conductive pathway 120), or any other coupling mechanism described herein, and (b) the first fabric portion is disposed between the second fabric portion and the third fabric portion. The first, second, and third fabric portions can be formed a non-conductive yarn, for example, any non-conductive yarn described herein. In such embodiments, the second fabric portion and third fabric portion can be configured to electrically insulate the knitted conductive pathway 120 from the skin of the user U as well as the outside environment. In some embodiments, the knitted conductive pathway can also be insulated with a laminating or insulating layer, as described herein. In some embodiments, the system 100 can include a stitch, for example, a first stitch, configured to couple the second fabric portion to the first fabric portion along or otherwise proximate to the second fold line such that the second fabric portion remains proximate to the first fabric portion during use. Furthermore, the system 100 can include a second stitch configured to couple the third fabric portion to the first fabric portion and the second fabric portion along the first fold line such that the third fabric portion remains proximate to the first fabric portion and the second fabric portion during use. In some embodiments, the first, second and third fabric portions can be substantially tubular, such that the system 100 resembles a tube, or a band.

In some embodiments, the system 100 can include a one layer band. The one layer band can include the electrode 110, the conductive pathway 120 and the connector 140 disposed thereon and configured to be coupled to the conductive pathway 120. In such embodiments, the conductive pathway 120 can be electrically insulated by a lamination layer, as described herein. In some embodiments, the electrode 110 and the conductive pathway can be knitted from conductive yarn. In some embodiments, the electrode 110 and the conductive pathway 120 can be printed, for example, using conductive ink.

In some embodiments, the system 100 can include a two layer band. In such embodiments, the system 100 can include an outer portion that can include the connector 140 disposed thereon and configured to be coupled to the conductive pathway 120, and a skin facing portion that includes the electrode 110. The conductive pathway 120 can be disposed in the outer portion and/or the skin facing portion, and disposed and configured to be electrically coupled to the electrode 110 and the connector 140, for example, disposed in an opening in the third fabric portion. In such embodiments, the conductive pathway 120 can be electrically insulated by the outer portion and the skin facing portion or a lamination, as described herein. In some embodiments, the two layer band can be configured such that the skin facing portion is folded along a first fold line and at least partially overlaps the outer portion. In some embodiments, the two layer band can be configured such that the skin facing portion is folded about the first fold line and is adjacent to but does not overlap the outer portion. In any of these embodiments, the conductive pathway can be coupled to the electrode using conductive yarn or conductive thread.

In some embodiments, the system 100 can be configured to have a tubular shape. In such embodiments, the system 100 can be configured to be used by the user U as a waist band, a head band, an arm band, a thigh band, a head band, a wrist band, or an ankle band. Furthermore, the system 100 can be included in a wearable garment, for example, a shirt, a jersey, a vest, a bra, or any other wearable garment. In some embodiments, the system 100 can have any other suitable shape or size and can be included in any suitable wearable garment, for example, a glove, a sock, a shoe, etc.

Having described above various general principles, several embodiments of these concepts are now described. These embodiments are only examples, and many other configurations of a textile-based electrode system are contemplated.

Figure 2:
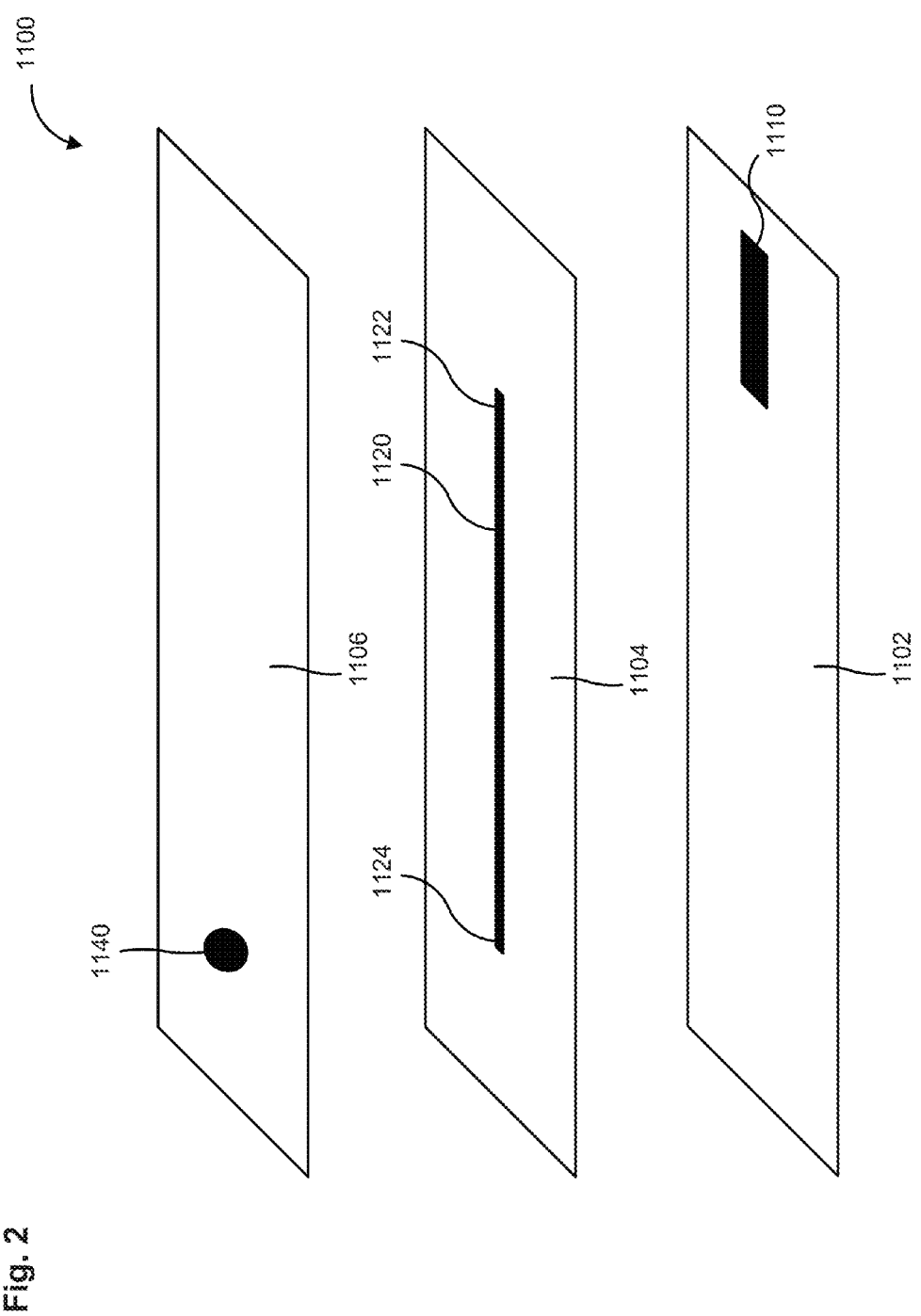
FIG. 2 is a schematic illustration of a textile-based electrode system that includes a first fabric layer, a second fabric layer, and a third fabric layer in a first configuration, according to an embodiment.
Figure 3:
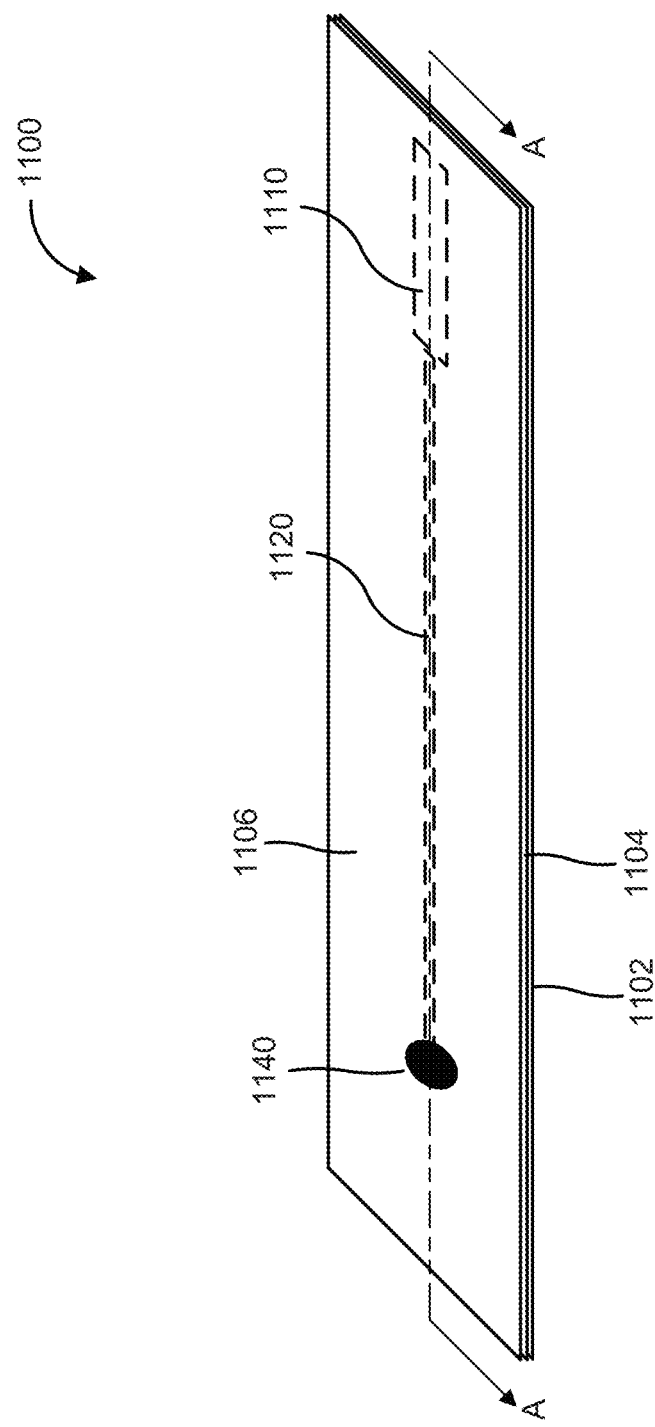
FIG. 3 shows the textile-based electrode system of FIG. 2 in a second configuration.
Figure 4:
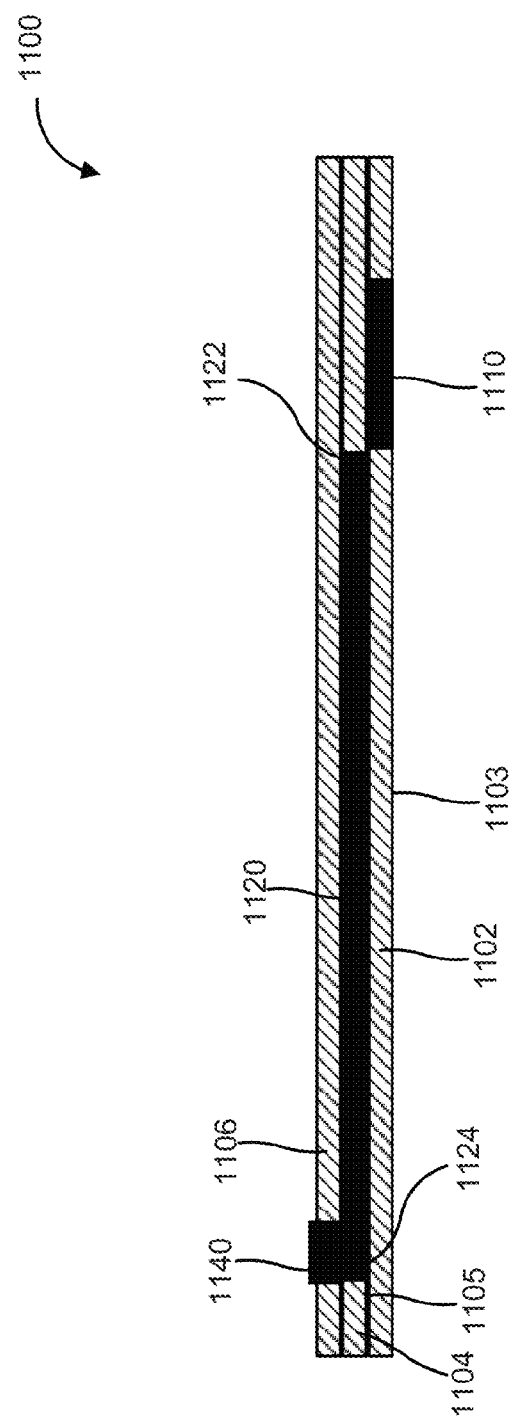
FIG. 4 shows a side cross-sectional view of the textile-based electrode system of FIG. 2 taken along the line A-A shown in FIG. 3.

In some embodiments, a textile-based electrode system can include a plurality of fabric layers. Referring now to FIGS. 2-4, a textile-based electrode system 1100 includes a first fabric layer 1102, a second fabric layer 1104, and a third fabric layer 1106. The first fabric layer 1102 includes a knitted electrode 1110, the second fabric layer 1104 includes a knitted conductive pathway 1120, and the third fabric layer 1106 includes a connector 1140. The textile-based electrode system 1100 is configured to be associated with a user, for example, worn by a user and sense one more physiological parameters of the user.

The first fabric layer 1102 can be formed from a non-conductive material such as, for example, nylon, cotton, silk, ramie, polyester, latex, spandex, any other suitable non-conductive yarn or combination thereof. Furthermore, the first fabric layer 1102 can be formed from a stretchable material, for example, to conform to the skin of the user and enable sufficient contact between the knitted electrode 1110 and the skin of the user. The first fabric layer 1102 includes an inner surface 1103 and an outer surface 1105 (FIG. 4). The inner surface 1103 includes the knitted electrode 1110 and is configured to be placed in the contact with the skin of the user such that the knitted electrode 1110 can measure an electrical signal corresponding to a physiological parameter of the user (e.g., a galvanic skin response (GSR), an electrocardiogram (ECG), a heart rate, a breathing rate, a breathing pattern, a rib cage perimeter, a rib cage volume, an electromyelogram, and a body temperature). The knitted electrode 1110 can be continuously and seamlessly knitted in the first fabric layer 1102. The knitted electrode 1110 can be formed from a conductive yarn such as, for example, XSTATIC® silver metalized yarn, stainless steel thread, SCHOELLER® wool, polyaniline yarn, any other suitable conductive yarn or a combination thereof. In some embodiments, a padding member can be disposed on the outer surface 1105 of the first fabric layer 1102 adjacent to the knitted electrode 1110. In some embodiments, the padding member can be disposed between the first fabric layer 1102 and the second fabric layer 1104. In some embodiments, the padding member can be disposed between the second fabric layer 1104 and the third fabric layer 1106. The padding member can be formed from any suitable material such as, for example, rubbery foam, a sponge, memory foam, a 3-D knitted porous fabric (e.g., a 3-D knitted mesh or 3-D spacer knit), any other suitable material or combination thereof. In some embodiments, the padding member is configured to urge the knitted electrodes 1110 toward the skin of the user when in use to improve signal quality. While shown as having a square shape, the knitted electrode 1110 can have any suitable size or shape such as, for example, square, rectangular, circular, elliptical, oval, polygonal, any other suitable shape or size. In some embodiments, the first fabric layer 1102 can include a plurality of knitted electrodes 1110, for example, 2, 3, 4, 5 or even more.

The second fabric layer 1104 is configured to contact the outer surface 1105 of the first fabric layer 1102. The second fabric layer 1104 can be formed from substantially the same material as the first fabric layer 1102. The second fabric layer includes a knitted conductive pathway 1120 that includes a first end 1122 and a second end 1124. The knitted conductive pathway 1120 is configured to be coupled to the knitted electrode 1110, as described herein. The knitted conductive pathway 1120 can be formed from substantially the same material as the knitted electrode 1110. While shown as including a single knitted conductive pathway 1120, any number of knitted conductive pathways can be included in the second fabric layer 1104, for example, 2, 3, 4, 5, or even higher corresponding to the number of knitted electrodes 1110 included in the first fabric layer 1102.

In some embodiments, an insulating member can be disposed on at least a portion of the knitted conductive pathway 1120. The insulating member can be disposed one side or both sides of the knitted conductive pathway 1120 by laminating or overprinting a suitable insulating material such as, for example, a heat sealed adhesive, an insulating membrane, silicon, plastic, polymer, mica, etc over the knitted conductive pathway 1120. The insulating material can, for example, reduce signal noise and thereby, improve signal quality. In some embodiments, the insulating member can also be configured to provide a moisture impervious barrier, for example, to prevent electrical shorts.

The third fabric layer 1106 is configured to contact the second fabric layer. The third fabric layer 1106 can be formed from substantially the same material as the first fabric layer 1102. The connector 1140 is disposed on the third fabric layer 1106 and is configured to be electrically coupled to the knitted conductive pathway 1120. The connector 1140 can, for example, be disposed in an opening defined in the third fabric portion 1106. The connector 1140 can be coupled to the knitted conductive pathway using any suitable means, for example, mechanical coupling, stitching or sewing with conductive yarn, with conductive adhesive or epoxy, hot wire press, high frequency welding, ultrasonic welding, any other suitable coupling mechanism or combination thereof. While shown as being disposed on the third fabric layer 1106, in some embodiments, the connector 1140 can disposed on the second fabric layer 1104 and electrically coupled to the knitted conductive pathway 1120. The connector can include a snap-fit connector (e.g., a male or female connector, a pin socket connector, a DIN connector, a banana connector), a hook connector, a magnetic connector, any other suitable connector or a combination thereof. The connector can be configured to be removably coupled to a connector assembly (e.g., the connector assembly 160 or any other connector assembly described herein) such that the knitted connector region (and thereby the electrode 1110) is in electrical communication with the connector assembly. At least a portion of the connector 1140, for example, the portion of the connector 1140 coupled to the knitted conductive pathway 1120 can be insulated with an insulating material, as described herein. While shown as including a single connector 1140, the third fabric portion can include any number of connectors 1140, for example, 2, 3, 4, 5, or even more (e.g., corresponding to the number of electrode 1110 included in the system 1100).

In some embodiments, the third fabric layer 1106 can include a knitted connector region configured to be electrically coupled to at least one of the knitted conductive pathway 1120 and the connector 1140. The knitted connector region can be configured to be electrically coupled to the knitted conductive pathway 1120, for example, using conductive yarn. The knitted connector region can be formed from substantially the same material as the knitted electrode 1110.

FIG. 2 shows the system 1110 in a first configuration in which the first fabric layer 1102, the second fabric layer 1104, and the third fabric layer 1106 are separated from each other. In a second configuration, the second fabric layer 1104 can be disposed on the outer surface 1105 of the first fabric layer 1102, and the third fabric layer 1106 can be disposed on the second fabric layer 1104 as shown in FIG. 3. In the second configuration, the inner surface 1103 of the first fabric portion is configured to contact the skin of the user such that the electrode 1110 contacts the skin of the user during use. As shown in the side-cross section view of FIG. 4, the knitted conductive pathway 1120 is disposed between the first fabric layer 1102 and the third fabric layer 1106 in the second configuration. In this manner, the first fabric layer 1102 electrically insulates the second fabric layer 1104 from a skin of the user and the third fabric layer 1106 electrically insulates the second fabric layer 1104 from the outside environment.

Furthermore, the first end 1122 of the knitted conductive pathway 1120 can be disposed adjacent to but not contacting or otherwise overlapping the knitted electrode 1110 in the second configuration, as shown in FIG. 4. In such embodiments, the first end 1122 of the knitted conductive pathway 1120 can be electrically coupled to the knitted electrode 1110 using conductive yarn or gluing (e.g., by conductive glue or conductive epoxy). Moreover, the second end 1124 of the knitted conductive pathway 1120 can be at least partially overlapping the connector 1140, such that the second end 1124 knitted conductive pathway 1120 can be electrically coupled to the connector 1140 (e.g., by mechanical coupling, stitching or sewing with conductive yarn, or conductive adhesive). In this manner, the knitted electrode 1110 can be in electrical communication with the connector 1140 via the knitted conductive pathway 1120 and the connector 1140 in the second configuration In some embodiments, the first end 1122 and/or the second end 1124 of the knitted conductive pathway 1120 can be configured to at least partially overlap the knitted electrode 1110 in the second configuration. In such embodiments, the first end 1122 of the knitted conductive pathway 1120 can be configured to be coupled to the knitted electrode 1110 using any suitable means such as for example, stitching or sewing with a conductive yarn, gluing (e.g., with a conductive glue or conductive epoxy), hot wire press, high frequency welding, ultrasonic welding, or any other suitable coupling mechanism. In some embodiments, the third fabric layer 1106 can include a conductive connector region (not shown) configured to be electrically coupled to the second end 1124 of the knitted conductive pathway 1120 as described herein.

While shown as being separate fabric layers, in some embodiments, the first fabric layer 1102 can be continuously formed (e.g., seamlessly coupled) with the second fabric layer 1104. Furthermore, the second fabric layer 1104 can be continuously formed (e.g., seamlessly coupled) with the third fabric layer 1106 such that the textile-based electrode system 1110 is a single piece textile blank. In such embodiments, the second fabric layer 1104 can be folded about a first fold axis to place the second fabric layer 1104 in contact with the outer surface 1105 of the first fabric layer 1102. Moreover, the third fabric layer 1106 can be folded about a second fold axis to place the third fabric layer 1106 in contact with the second fabric layer 1104, thereby placing the system 1110 in the second configuration. The first fabric layer 1102 can be coupled to the second fabric layer 1104 and the third fabric layer 1106 along at least one of the first fold axis and the second fold axis (e.g., by stitching, sewing, gluing, hot wire press, high frequency welding, ultrasonic welding, etc.) such that the second fabric layer 1104 and the third fabric layer 1106 are maintained in the second configuration (i.e., in a folded state).

In some embodiments, a first insulating member can be disposed between the first fabric layer 1102 and the second fabric layer 1104. Furthermore, a second insulating member can be disposed between the second fabric layer 1104 and the third fabric layer 1106. The first and second insulating members can be configured to electrically and mechanically isolate the knitted conductive pathway 1120 from the first fabric layer 1102 and the second fabric layer 1104. This can reduce signal noise and thereby, enhance overall signal quality. In some embodiments, the first and second insulating members can also be configured to provide a moisture impervious barrier, for example, to prevent electrical shorts.

In some embodiments, a textile-based electrode system can include a plurality of portions. Referring now to FIGS. 5A-5G and FIG. 6, a textile-based electrode system includes a first fabric portion 1202, a second fabric portion 1204, a third fabric portion 1206. The first fabric portion 1202 includes a knitted conductive pathway 1220. The second fabric portion 1204 extends from the first fabric portion 1202 and includes a knitted electrode 1210. The third fabric portion 1206 extends from the second fabric portion 1204 and includes a connector region 1230 configured to be coupled to the knitted conductive pathway 1220 by a connector 1240. The textile-based electrode system 1210 is configured to be associated with a user, for example, worn by a user and sense one more physiological parameters of the user.

The first fabric portion 1202 can be formed from a non-conductive yarn, for example, any of the non-conductive yarns described herein. Furthermore, the first fabric portion 1202 can be formed from a stretchable material, for example, to conform to the skin of the user and enable sufficient contact between the knitted electrode 1210 and the skin of the user. The knitted conductive pathway 1220 can be continuously formed (e.g., seamlessly formed) in the first fabric portion 1202. The knitted conductive pathway 1220 can be formed from a conductive yarn, for example, any of the conductive yarns described herein.

The second fabric portion 1204 can be formed from substantially the same material as the first fabric portion 1202. The knitted electrode 1210 is configured to be placed in contact with the skin of the user, as described herein, such that the knitted electrode 1210 can measure an electrical signal corresponding to a physiological parameter of the user, for example, any of the physiological parameters described herein. The knitted electrode 1210 can be continuously and seamlessly knitted in the second fabric portion 1204. The knitted electrode 1210 can be formed from substantially the same material as the knitted conductive pathway 1220. While shown as having a square shape, the knitted electrode 1210 can have any suitable size or shape such as, for example, square, rectangular, circular, elliptical, oval, polygonal, any other suitable shape or size.

The third fabric portion 1206 can be formed from substantially the same material as the first fabric portion 1202. The connector region 1230 can include an opening defined in the third fabric portion 1206, for example, during knitting of the third fabric portion 1206 and/or otherwise formed in the third fabric 1206 after the knitting process. The connector 1240 can be disposed in the opening 1230 defined in the third fabric portion 1206 and can be configured to be electrically coupled to the knitted conductive pathway 1220 by any suitable method described herein (e.g., mechanical coupling). The connector 1240 can be substantially similar to the connector 140 or any other connector described herein. The connector 1240 can be configured to be removably coupled to a connector assembly (e.g., the connector assembly 160 or any other connector assembly described herein) such that the knitted conductive pathway 1220 (and thereby the electrode 1210) is in electrical communication with the connector assembly. In some embodiments, the connector 1240 can be disposed on the second fabric portion 1204 and electrically coupled to the knitted conductive pathway 1220.

In some embodiments, the connector region 1230 can include a conductive portion, for example, a knitted conductive portion configured to be electrically coupled to the knitted conductive pathway 1220. The conductive portion can be configured to be electrically coupled to the knitted conductive pathway 1220, for example, using conductive yarn. The conductive portion can be formed from substantially the same material as the knitted electrode 1110.

While shown as being substantially flat, in some embodiments, the first fabric portion 1202, the second fabric portion 1204, and the third fabric portion 1206 can be substantially tubular. Furthermore, the first fabric portion 1202, the second fabric portion 1204, and the third fabric portion 1206 can be formed seamlessly (e.g., knitted continuously).

Figure 5A:
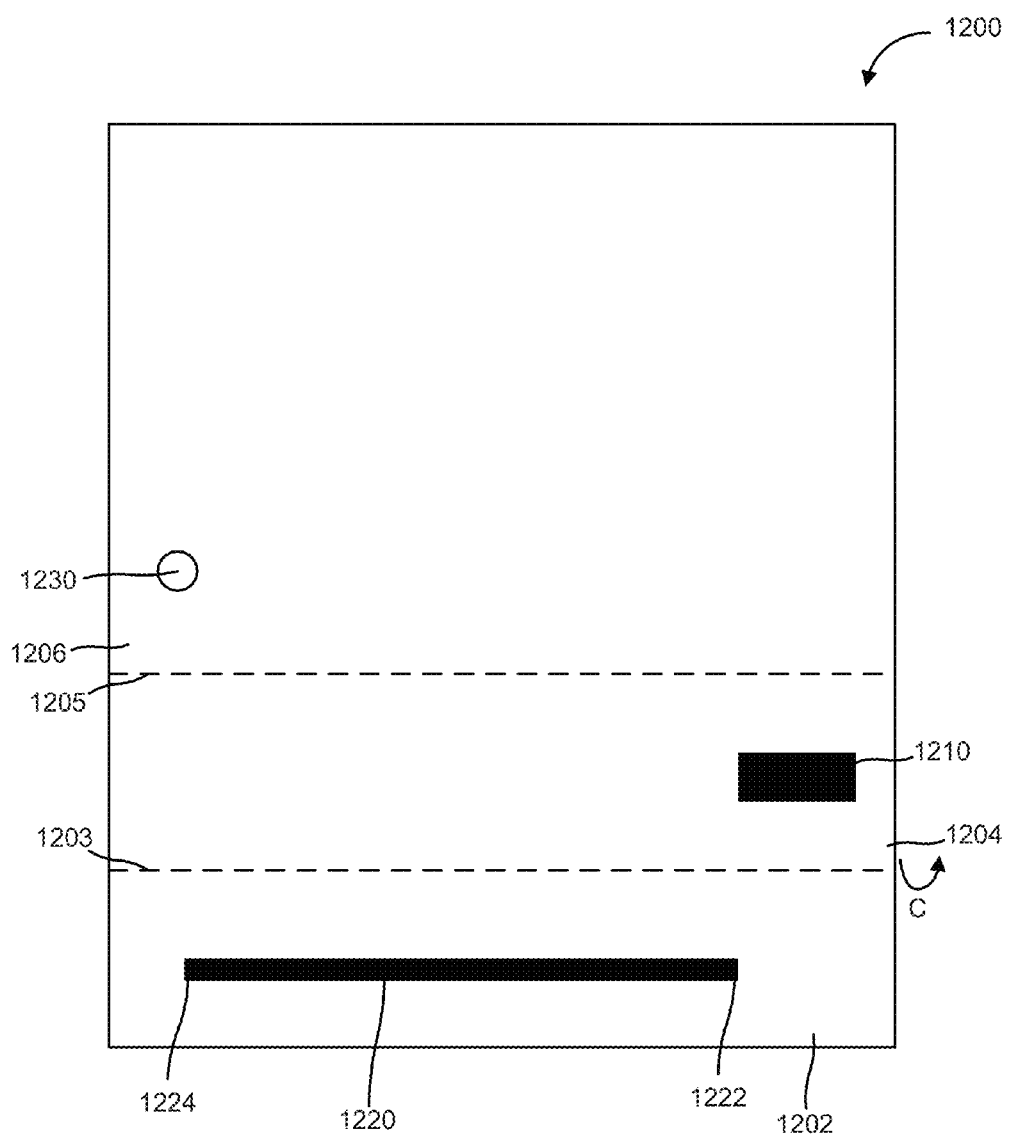
FIG. 5A shows a front view of a textile-based electrode system, according to an embodiment.
Figure 5C:
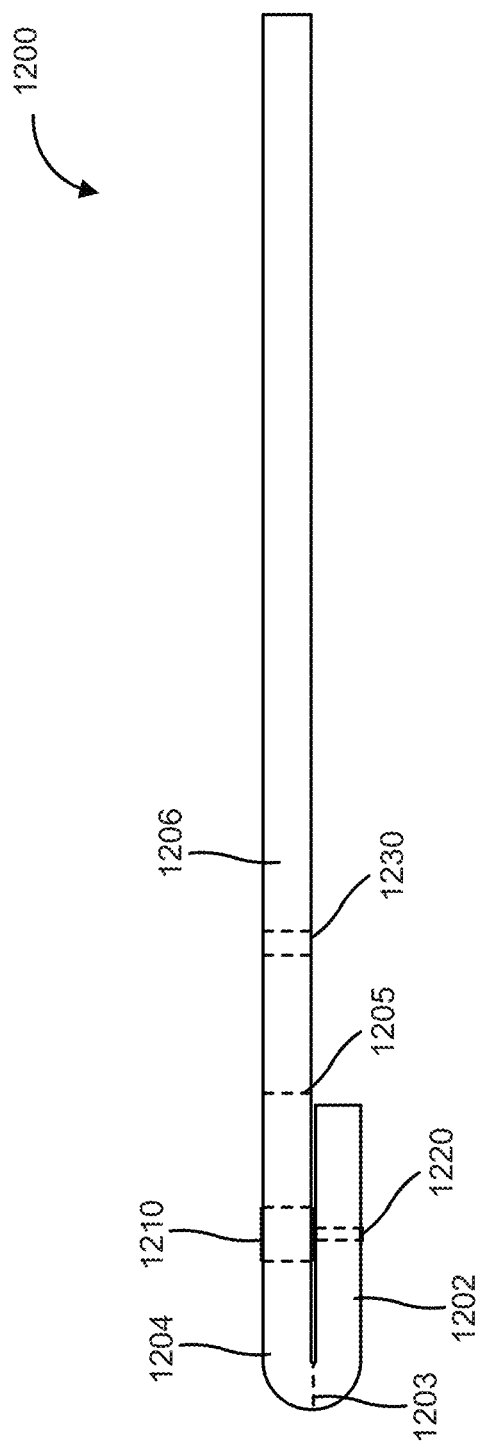
FIG. 5C shows a side view of the system with the first fabric portion fully folded along the first fold line.
Figure 5D:
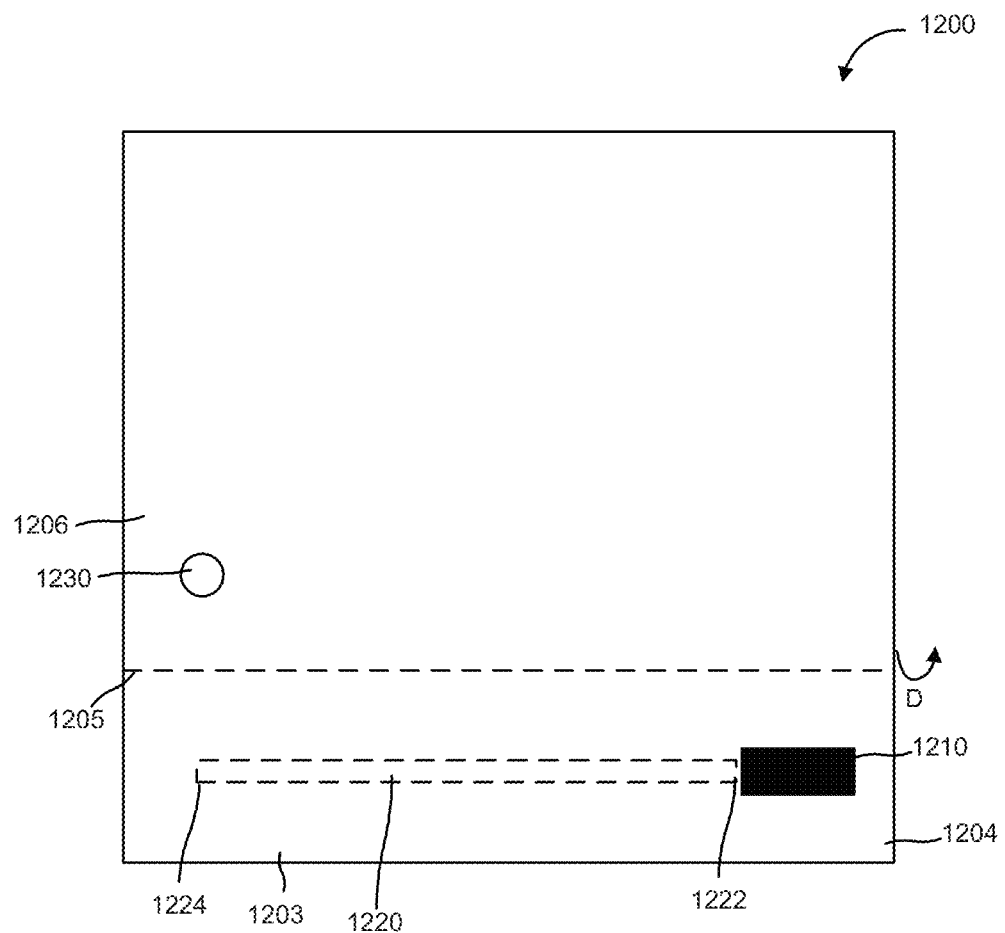
FIG. 5D shows a front view of the system shown in FIG. 5C.

The system 1200 can be moved from a first configuration in which the knitted electrode 1210 and the knitted conductive pathways 1220 are electrically isolated, to a second configuration in which the knitted conductive pathway 1220 is configured to be electrically coupled to the knitted electrode 1210, and finally to a third configuration in which the knitted conductive pathway 1220 is configured to be electrically coupled to the connector 1240. FIG. 5A shows the system 1200 in the first configuration. In the first configuration, neither one of the first fabric portion 1202, the second fabric portion 1204, or the third fabric portion 1206 is folded. The first fabric portion 1202 can be folded along a first fold line 1203 in a direction shown by the arrow C to move the system 1200 from the first configuration to the second configuration. As shown in FIG. 5B, the first fabric portion 1202 is moved towards the second fabric portion 1204 until the first fabric portion 1202 is disposed adjacent to the second fabric portion 1204 (FIGS. 5C and 5D). Furthermore, a first end 1222 of the knitted conductive pathway 1220 is disposed adjacent to but not overlapping the knitted electrode 1210. In such embodiments, the first end 1222 of the knitted conductive pathway 1220 can be coupled to the knitted electrode 1210 by stitching or sewing with conductive yarn.

Figure 5E:
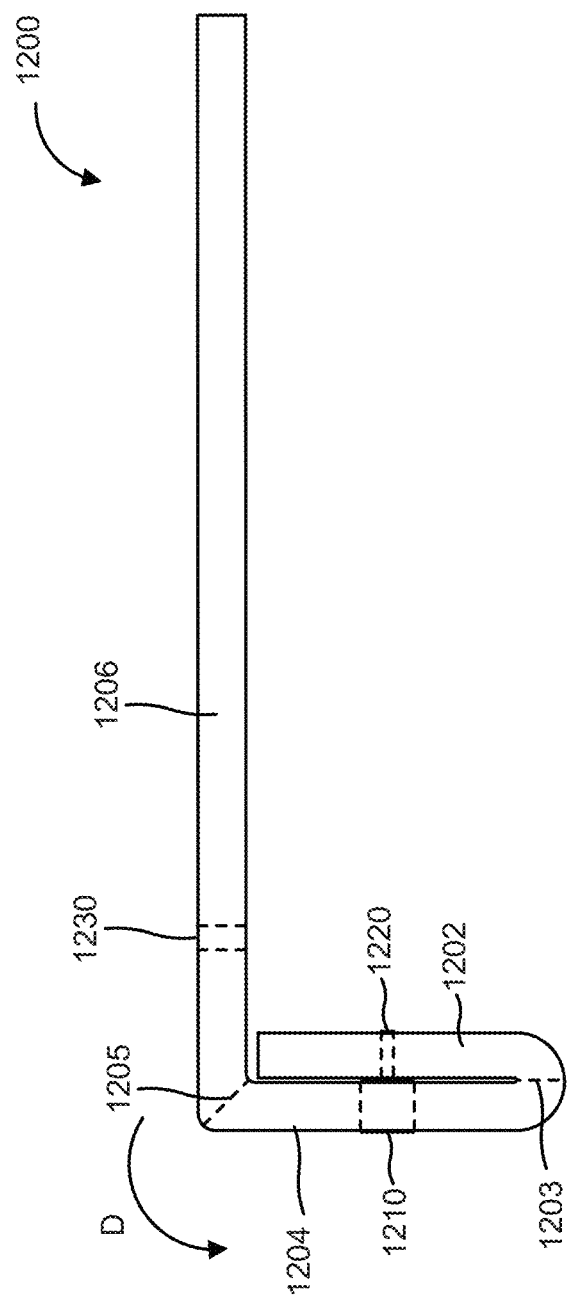
FIG. 5E shows a side view of the system with a second fabric portion of the system partially folded along a second fold line.
Figure 5F:
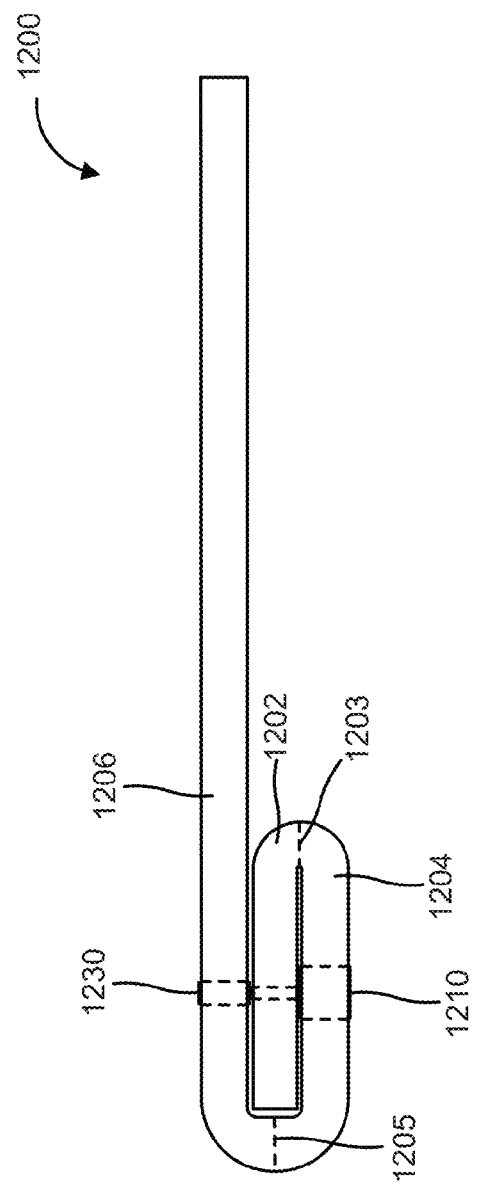
FIG. 5F shows a side view of the system with the second fabric portion fully folded along the second fold line.
Figure 5G:
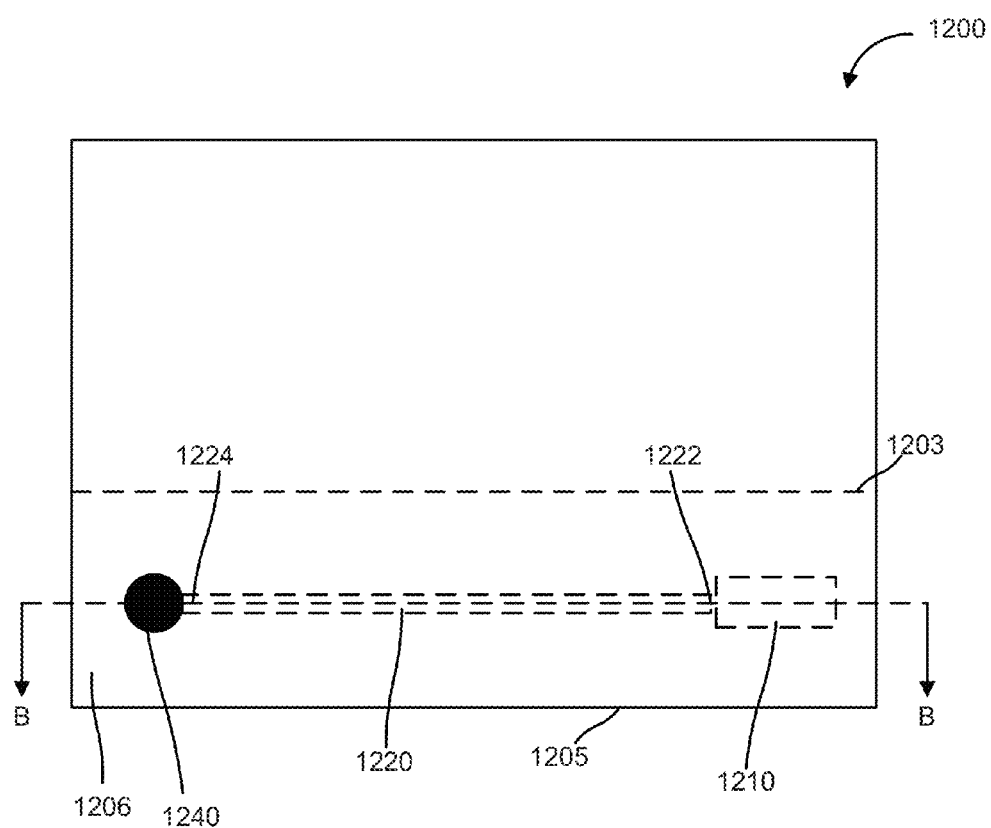
FIG. 5G shows a front view of the system shown in FIG. 5F.

The second fabric portion 1204 can then be folded about a second fold line 1205 in a direction shown by the arrow D (FIGS. 5D and 5E) to move the system 1200 from the second configuration to the third configuration. As shown in FIGS. 5D and 5E, the first fabric portion 1202 and the second fabric portion 1204 are moved towards the third fabric portion 1206, until the first fabric portion is disposed adjacent to the third fabric portion 1206 and the system 1200 is in the third configuration (FIGS. 5F and 5G). Furthermore, a second end 1224 of the knitted conductive pathway 1220 can overlap the connector region 1230. The connector 1240 can be disposed in the connector region 1230 and electrically coupled to the knitted conductive pathway 1220, for example, using mechanical coupling, conductive adhesive or any other coupling mechanism described herein.

While shown as being adjacent and not overlapping in some embodiments, the first end 1222 of the knitted conductive pathway 1220 can be configured to at least partially overlap the knitted electrode 1210 after folding the first fabric portion 1202 about the first fold line 1203. In such embodiments, first end 1222 of the knitted conductive pathway 1220 can be coupled to the knitted electrode 1210 by stitching or sewing with conductive yarn, gluing with conductive adhesive or epoxy, hot wire press, high frequency welding, ultrasonic welding, any other suitable coupling mechanism or combination thereof.

Figure 6:
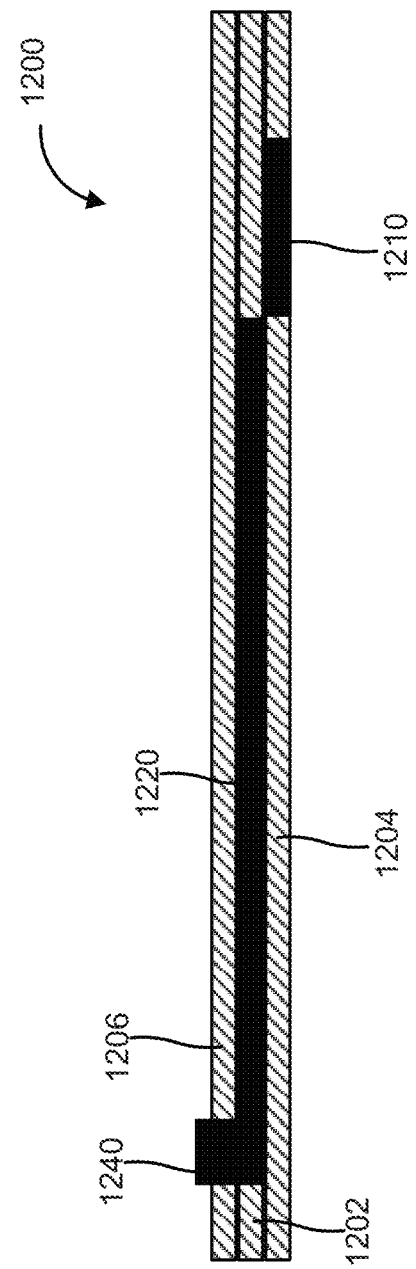
FIG. 6 shows a side cross-section view of the system of FIG. 5G taken along the line B-B as shown in FIG. 5G.

As shown in FIG. 6, in the second configuration, the knitted conductive pathway 1220 can be disposed between the second fabric portion 1204, and third fabric portion 1206. In this way, the knitted conductive pathway 1220 can be electrically insulated from the skin of the user by the second fabric portion 1204, and electrically insulated from the outside environment by the third fabric portion 1206. In some embodiments, the system 1200 can include a first stitch configured to couple the second fabric portion 1204 to the first fabric portion 1202 such that the second fabric portion 1204 remains proximate to the first fabric portion 1202 during use. Furthermore, the system 1200 can also include a second stitch configured to couple the third fabric portion 1206 to the first fabric portion 1202 and the second fabric portion 1204 such that the third fabric portion 1206 remains proximate to the first fabric portion 1202 and the second fabric portion 1204 during use. Said another way, the first stitch and the second stitch can ensure that the first fabric layer 1202 remains folded about the first fold line 1203, and the second fabric layer 1204 remains folded about the second fold line 1205 such that the system 1200 is maintained in the second configuration during use.

In some embodiments, a padding member (not shown) can be disposed between the first fabric portion 1202 and the second fabric portion 1204 adjacent to the knitted electrode 1210. In some embodiments, the padding member can be disposed on the first fabric portion 1202 while the system 1200 is in the first configuration. In some embodiments, the padding member can be disposed on the first fabric portion 1202 while the system is 1200 being moved from the first configuration into the second configuration. In some embodiments, the padding member can be disposed between the first fabric portion 1202 and the second fabric portion 1204 when the system is in the second configuration. In some embodiments, the padding member can be disposed between the second fabric portion 1204 and the third fabric portion 1206 adjacent to the first end 1222 of the knitted conductive pathway 1220, such that the padding member is adjacent to the knitted electrode 1210. In such embodiments, the padding member can be disposed between the second fabric portion 1204 and the third fabric portion 1206 when the system 1200 is in the second configuration, or while the system 1200 is being moved from the second configuration to the third configuration. The padding member can be formed from any suitable material such as, for example, rubbery foam, a sponge, memory foam, a 3-D knitted porous fabric (e.g., a 3-D knitted mesh or 3-D spacer knit), any other suitable material or combination thereof. In some embodiments, the padding member is configured to urge the knitted electrode 1210 toward the skin of the user when in use to improve signal quality.

In some embodiments, an insulating member can be disposed between the first fabric portion 1202 and the second fabric portion 1204, and/or between the second fabric portion 1204 and the third portion 1206. For example, in some embodiments, a first insulating member can be disposed between the first fabric portion 1202 and the second fabric portion 1204. The first insulating member can be configured to electrically and/or mechanically isolate the knitted conductive pathway 1220 from the second fabric layer 1204. The first insulating member can be disposed while the system 1200 is in the first configuration. In some embodiments, the first insulating member can be disposed while the system 1200 is being moved from the first configuration to the second configuration. Moreover, a second insulating member can be disposed between the first fabric portion 1202 and the third fabric portion 1206. The second insulating member can be configured to electrically and/or mechanically isolate the knitted conductive pathway 1220 from the third fabric layer 1206. The second insulating member can be disposed while the system 1200 is in the first configuration. In some embodiments, the second insulating member can be disposed while the system 1200 is being moved from the first configuration to the second configuration, while the system 1200 is in the second configuration, while the system 1200 is being moved from the second configuration into the third configuration. The electrical and/or mechanical insulation provided by the first and second insulating members can reduce signal noise and thereby, enhance overall signal quality. In some embodiments, the first and second insulating members can also be configured to provide a moisture impervious barrier, for example, to prevent electrical shorts.

Figure 7:
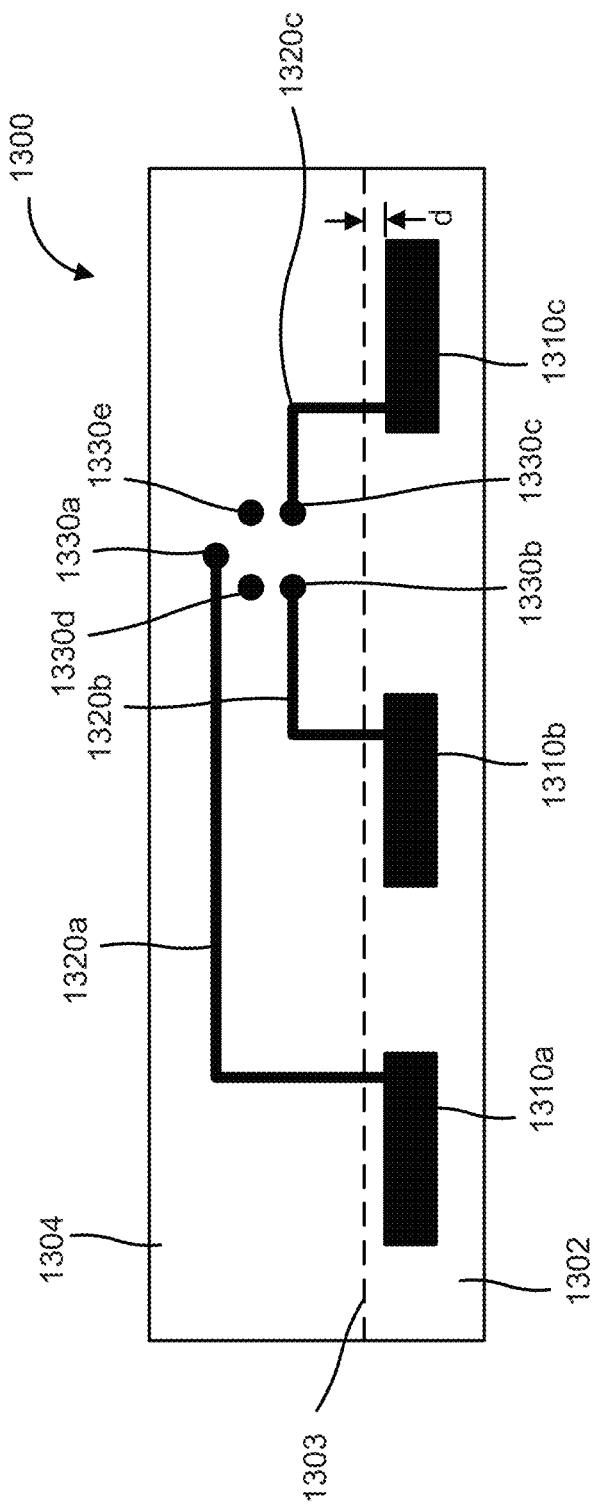
FIG. 7 shows a front view of a textile-based electrode system that includes a textile blank, according to an embodiment.

In some embodiments, a textile-based electrode system can include a plurality of electrodes. Referring now to FIG. 7, a textile-based electrode system 1300 can include a textile blank that includes a skin facing portion 1302 and an outer portion 1304. The skin facing portion 1302 includes a first electrode 1310a, a second electrode 1310b, a third electrode 1310c (collectively referred to as "the electrodes 1310") and at least a portion of a first conductive pathway 1320a, a second conductive pathways 1320b and a third conductive pathway 1320c (collectively referred to as "the conductive pathways 1320"). The outer portion 1304 extends from the skin facing portion 1302 and includes a first connector region 1330a, a second connector region 1330b, a third connector region 1330c, a fourth connector region 1330d, a fifth connector region 1330e (collectively referred to as "the connector regions 1330"), and at least a portion of the conductive pathways 1320 which extend from the skin facing portion 1302 into the outer portion 1304. The system 1300 can be included in any textile or garment, for example, a band, a shirt, a jersey, a vest, a bra, or any other wearable textile, such that, the system 1300 can measure one or more physiological parameters of a user.

The skin facing portion 1302 and the outer portion 1304 can be formed from a non-conductive material, for example, any of the materials described with respect to the first fabric layer included in the textile-based electrode system 100. Furthermore, the skin facing portion 1302 can be continuously formed with the outer portion 1304 (e.g., seamlessly coupled). The skin facing portion 1302 is configured to folded about a fold line 1303 such that the skin facing portion 1302 overlaps the outer portion 1304 and is configured to contact the skin of the user during use. The system 1300 can include one or more stitches configured to couple the skin facing portion 1302 to the outer portion 1304, such that the skin facing portion 1302 remains proximate to the outer portion 1304 during use. The electrodes 1310 can be continuously and seamlessly knitted with the skin facing portion 1302. The electrodes 1310 are substantially aligned with each other such that a top edge of each of the electrodes 1310 is disposed at a distance d from the fold line 1303. The electrodes 1310 can be formed from a conductive material, for example, knitted using conductive yarn, or printed with conductive ink. The electrodes 1310 can be substantially similar to the electrode 110, 1110, 1210, or any other electrode described herein and is therefore, not described in further detail herein. The electrodes 1310 are configured to contact the skin of a user and sense an electrical signal corresponding to one or more physiological parameters of the user. In some embodiments, any two of the electrodes 1310 (e.g., the first electrode 1310a and the second electrode 1310b) can be used to measuring the signals which are used to determine the physiological parameter of the user. In such embodiments, the remaining electrode 1310 (e.g., the third electrode 1310c) can be used to increase redundancy and robustness of the measurement, reduce noise, and/or amplify signals. While shown as including three electrodes 1310, any number of electrodes can be included in the skin facing portion 1302, for example, 2, 4, 5, 6 or even more.

The conductive pathways 1320 can be substantially similar to the conductive pathway 120, 1120, 1220, or any other conductive pathway described herein. The conductive pathways 1320 are seamlessly and continuously coupled to the electrodes 1310 using conductive yarn along a top edge of the electrodes 1310 proximal to the fold line 1303. The conductive pathways 1320 extend from the skin facing portion 1302 into the outer portion 1304 and are seamlessly and continuously knitted to the connector regions 1330. In this manner, the electrodes 1310 can be in electrical communication with the connector region 1330 via the conductive pathways 1320. The conductive pathways 1320 can be electrically insulated from the skin of the user and the outside environment by laminating or otherwise coating with an insulating material such as, for example, heat sealed adhesive, insulating membrane, polymers, plastic, mica, etc.

The connector regions 1330 are seamlessly and continuously knitted into the outer portion 1304 and coupled to the conductive pathways 1320 as described herein. While not shown, a connector, as described with respect to the system 100, 1100, 1200 or any other system described herein, can be coupled to each connector region 1330. The connectors can be configured to couple the connector regions 1330 to a connector assembly, for example, the connector assembly 160, or any other connector assembly described herein. As shown herein, the fourth connector regions 1330d and the fifth connector regions 1330e are not coupled to any conductive pathway 1320 and are thereby electrically isolated from the electrodes 1310. In some embodiments, the fourth connector regions 1330d and the fifth connector region 1330e can be configured to be coupled to a respiration sensor, for example, a respiration sensor included in the system 1300 or part of a separate system. Furthermore, connectors coupled to the connector regions 1330d and 1330e can ensure proper alignment of the connector assembly to the connector regions 1330.

In some embodiment, the connector regions 1330 can include openings configured to receive the connector. In such embodiments, the connectors can be electrically coupled to the conductive pathways 1320, for example, using mechanical coupling or a conductive adhesive.

Figure 8:
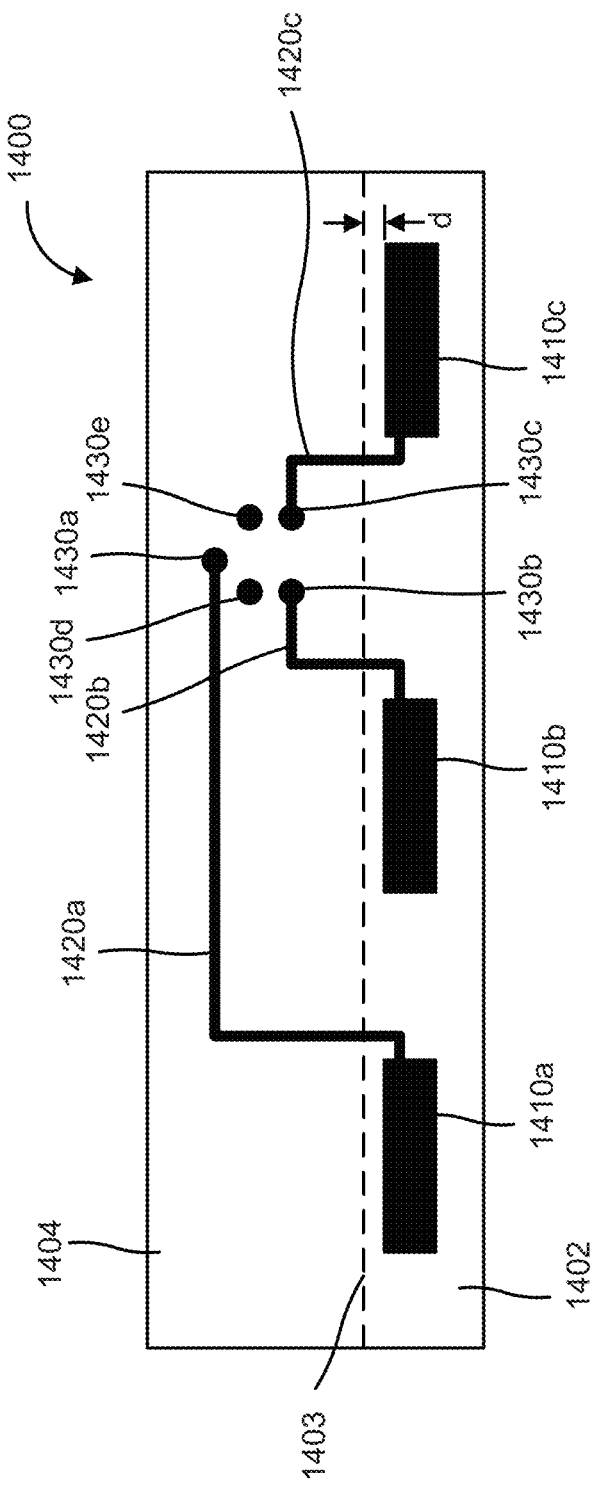
FIG. 8 shows a front view of a textile-based electrode system that includes a textile blank, according to an embodiment.

In some embodiments, a textile-based electrode system can include a plurality of electrodes that include conductive pathways electrically coupled to a side edge of the electrode. Referring now to FIG. 8, a textile-based electrode system 1400 includes a textile blank that includes a skin facing portion 1402 and an outer portion 1404. The skin facing portion 1402 includes a first electrode 1410a, a second electrode 1410b, a third electrode 1410c (collectively referred to as "the electrodes 1410") and at least a portion of a first conductive pathway 1420a, a second conductive pathway 1420b, and a third conductive pathway 1420c (collectively referred to as "the conductive pathways 1420"). The outer portion 1404 extends from the skin facing portion 1402, and includes a first connector region 1430a, a second connector region 1430b, a third connector region 1430c, a fourth connector region 1430d, a fifth connector region 1430e (collectively referred to as "the connector regions 1430"), and at least a portion of the conductive pathways 1420 which extend from the skin facing portion 1402 into the outer portion 1404. The system 1400 can be included in any textile or garment, for example, a band, a shirt, a jersey, a vest, a bra, or any other wearable textile, such that, the system 1400 can be used to measure one or more physiological parameters of a user.

The skin facing portion 1402 and the outer portion 1404 can be formed from a non-conductive material, for example, any of the materials described with respect to the first fabric layer included in the textile-based electrode system 100. Furthermore, the skin facing portion 1402 can be continuously formed with the outer portion 1404 (e.g., seamlessly coupled). The skin facing portion 1402 is configured to be folded about a fold line 1403 such that the skin facing portion 1402 overlaps the outer portion 1404 and is configured to contact the skin of the user during use. The system 1400 can include one or more stitches configured to couple the skin facing portion 1402 to the outer portion 1404, such that skin facing portion 1402 remains proximate to the outer portion 1404 during use. The electrodes 1410 can be continuously and seamlessly knitted into the skin facing portion 1402. The electrodes 1410 are substantially aligned with each other such that a top edge of each of the electrodes 1410 is disposed at a distance d from the fold line 1403. The electrodes 1410 can be formed from a conductive material, for example, conductive yarn. The electrodes 1410 can be substantially similar to the electrode 110, 1110, 1210, 1310, or any other electrode described herein and are therefore not described in further detail herein. The electrodes 1410 are configured to contact the skin of a user and sense an electrical signal corresponding to one or more physiological parameters of the user. While shown as including three electrodes 1410, any number of electrodes can be included in the skin facing portion 1402, for example, 2, 4, 5, 6 or even more, as described with respect to the electrodes 1310 included in the system 1300.

The conductive pathways 1420 can be substantially similar to the conductive pathway 120, 1120, 1220, 1320, or any other conductive pathway define herein. The conductive pathways 1420 are seamlessly and continuously knitted to the electrodes 1410 using conductive yarn along a side edge of the electrodes 1410 proximal to the other electrodes 1410. The conductive pathways 1420 extend from the skin facing portion 1402 into the outer portion 1404 and are seamlessly and continuously knitted to the connector regions 1430. In this manner, the electrodes 1410 can be in electrical communication with the connector region 1430 via the conductive pathways 1420. The conductive pathways 1420 can be electrically insulated from the skin of the user and the outside environment by laminating or otherwise coating with an insulating material such as, for example, heat sealed adhesive, insulating membrane, polymers, plastic, mica, etc.

The connector regions 1430 are seamlessly and continuously knitted into the outer portion 1404 and coupled to the conductive pathways 1420 as described herein. While not shown, connectors, as described with respect to the system 100, 1100, 1200, 1300, or any other system described herein, can be coupled to each connector region 1430. The connectors can be configured to couple the connector regions 1430 to a connector assembly, for example, the connector assembly 160, or any other connector assembly described herein. The connector regions 1430 can be substantially similar to the connector regions 130, 1130, 1230, 1330, or any other connector regions described herein, and are therefore not described in further detail herein.

In some embodiment, the connector regions 1430 can include openings configured to receive the connector. In such embodiments, the connectors can be electrically coupled to the conductive pathways 1420, for example, using mechanical coupling or a conductive adhesive.

Figure 9:
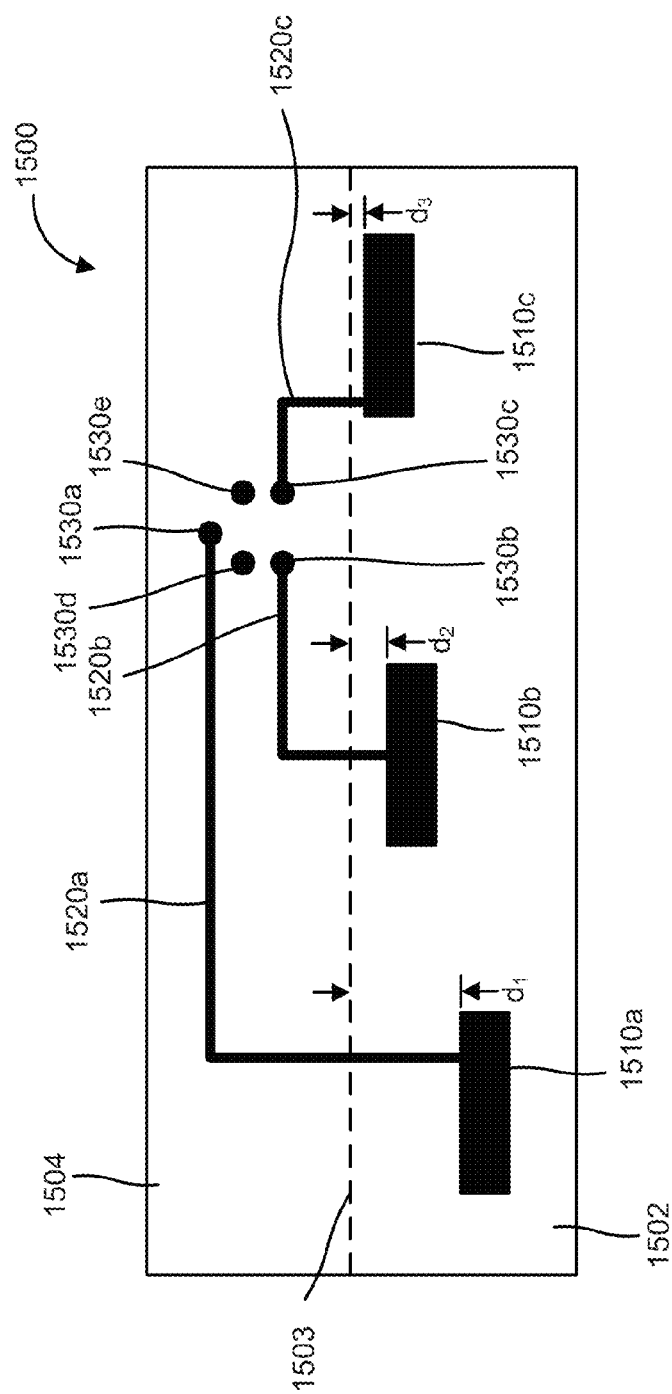
FIG. 9 shows a front view of a textile-based electrode system that includes a textile blank, according to an embodiment.

In some embodiments, a textile-based electrode system can include a plurality of electrodes that are not aligned with each other. Referring now to FIG. 9, a textile-based electrode system 1500 can include a textile blank that includes a skin facing portion 1502 and an outer portion 1504. The skin facing portion 1502 includes a first electrode 1510a, a second electrode 1510b, a third electrode 1510c (collectively referred to as "the electrodes 1510"), and at least a portion of a first conductive pathway 1520a, a second conductive pathway 1520b, and a third conductive pathway 1520c (collectively referred to as "the conductive pathways 1520"). The outer portion 1504 extends from the skin facing portion 1502 and includes a first connector region 1530a, a second connector region 1530b, a third connector region 1530c, a fourth connector region 1530d, a fifth connector region 1530e (collectively referred to as "the connector regions 1530"), and at least a portion of the conductive pathways 1520 which extend from the skin facing portion 1502 into the outer portion 1504. The system 1500 can be included in any textile or garment, for example, a band, a shirt, a jersey, a vest, a bra, or any other wearable textile, such that, the system 1500 can be used to measure one or more physiological parameters of a user.

The skin facing portion 1502 and the outer portion 1504 can be formed from a non-conductive material, for example, any of the materials described with respect to the first fabric layer included in the textile-based electrode system 100. Furthermore, the skin facing portion 1502 can be continuously formed with the outer portion 1504 (e.g., seamlessly coupled). The skin facing portion 1502 is configured to be folded about a fold line 1503 such that the skin facing portion 1502 overlaps the outer portion 1504 and is configured to contact the skin of the user during use. The system 1500 can include one or more stitches configured to couple the skin facing portion 1502 to the outer portion 1504, such that the skin facing portion 1502 remains proximate to the outer portion 1504 during use. The electrodes 1510 can be continuously and seamlessly knitted into the skin facing portion 1302. A first top edge of the first electrode 1510a is disposed at a first distance $d_1$ from the fold line 1503, a second top edge of the second electrode 1510b is disposed at a second distance $d_2$ from the fold line 1503, and a third top edge of the third electrode 1510c is disposed at a third distance $d_3$ from the fold line 1503, the first distance $d_1$, the second distance $d_2$, and the third distance $d_3$ different from each other. In this manner, the electrodes 1510 are located in the first portion 1502 such that they are misaligned. Furthermore, the electrodes 1510 can be configured to contact different portions of the skin of the user for example, the chest, back, near the bottom of the heart, the midriff, etc. In this way, the electrodes 1510 can measure key physiological signals from different portions of the skin of the user. The electrodes 1510 can be formed from a conductive material, for example, conductive yarn. The electrodes 1510 can be substantially similar to the electrode 110, 1110, 1210, 1310, or any other electrode described herein and are therefore, not described in further detail herein.

The conductive pathways 1520 can be substantially similar to the conductive pathway 120, 1120, 1220, 1320, or any other conductive pathway define herein. The conductive pathways 1520 are seamlessly and continuously knitted to the electrodes 1510 using conductive yarn. The conductive pathways 1520 extend from the skin facing portion 1502 into the outer portion 1504 and are seamlessly and continuously knitted to the connector regions 1530. In this manner, the electrodes 1510 can be in electrical communication with the connector region 1530 via the conductive pathways 1520. The conductive pathways 1520 can be electrically insulated from the skin of the user and the outside environment by laminating or otherwise coating with an insulating material such as, for example, heat sealed adhesive, insulating membrane, polymers, plastic, mica, etc.

The connector regions 1530 are seamlessly and continuously knitted into the outer portion 1504 and coupled to the conductive pathways 1520 as described herein. While not shown, a connector, as described with respect to the system 100, 1100, 1200, 1300, or any other system described herein, can be coupled to each connector region 1530. The connectors can be configured to couple the connector regions 1530 to a connector assembly, for example, the connector assembly 160, or any other connector assembly described herein. The connector regions 1530 can be substantially similar to the connector regions 130, 1130, 1230, 1330, or any other connector region described herein and are therefore, not described in further detail herein.

In some embodiment, the connector regions 1530 can include openings configured to receive the connector. In such embodiments, the connectors can be electrically coupled to the conductive pathways 1520, for example, using mechanical coupling or a conductive adhesive.

Figure 10:
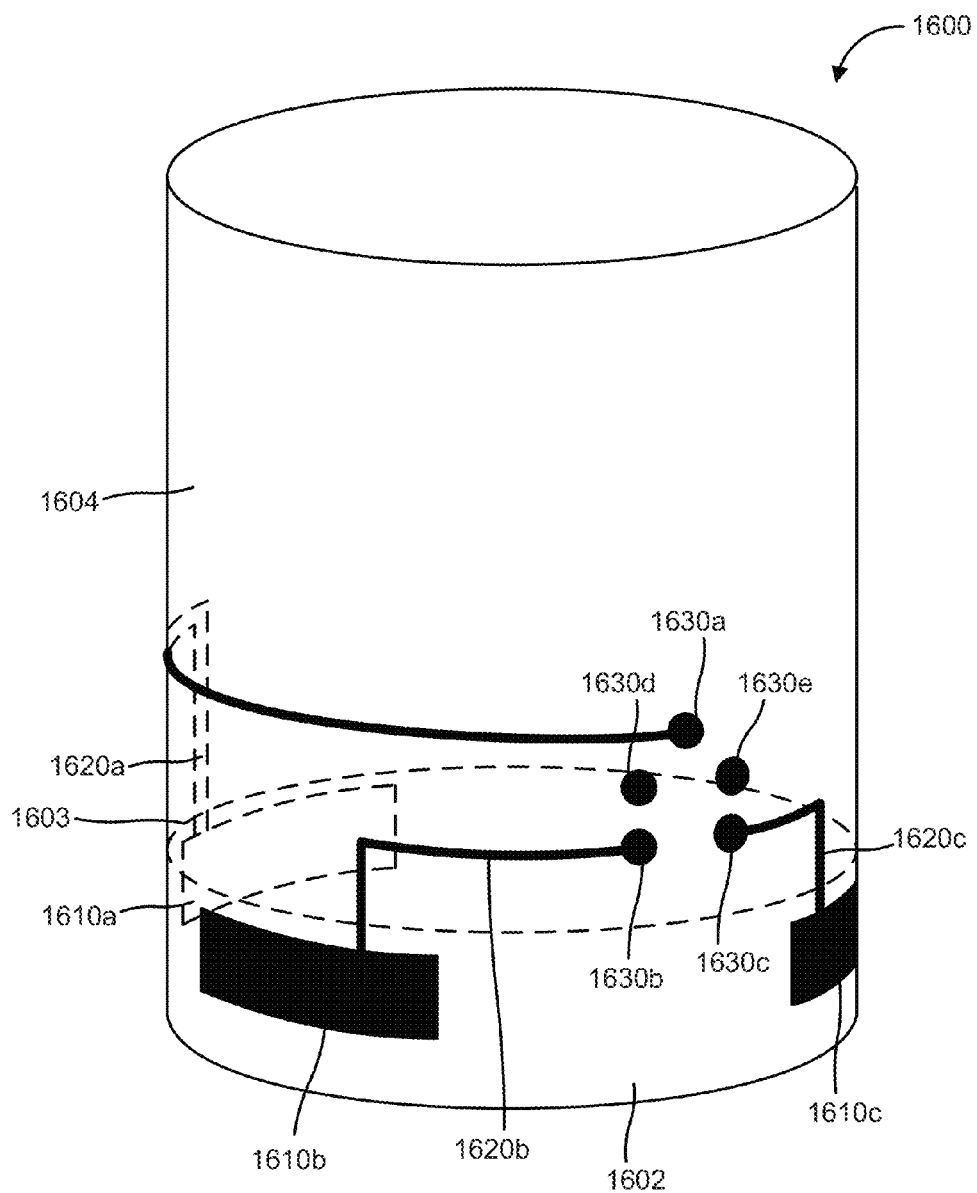
FIG. 10 shows a perspective view of a textile based electrode system that includes tubular portions, according to an embodiment.

In some embodiments, a textile-based electrode system can be substantially tubular. Referring now to FIG. 10, a textile-based electrode system 1600 includes a skin facing portion 1602 and an outer portion 1604. The skin facing portion 1602 includes a first electrode 1610a, a second electrode 1610b, a third electrode 1610c (collectively referred to as "the electrodes 1610"), and at least a portion of a first conductive pathway 1620a, a second conductive pathway 1620b, and a third conductive pathway 1620c (collectively referred to as "the conductive pathways 1620"). The outer portion 1604 extends from the skin facing portion 1602 and includes a first connector region 1630a, a second connector region 1630b, a third connector region 1630c, a fourth connector region 1630d, a fifth connector region 1630e (collectively referred to as "the connector regions 1630"), and at least a portion of the conductive pathways 1620, which extend from the skin facing portion 1602 into the outer portion 1604.

The skin facing portion 1602 and the outer portion 1604 can be formed from a non-conductive material, for example, any of the materials described with respect to the first fabric layer included in the textile-based electrode system 100. Furthermore, the skin facing portion 1602 can be continuously formed with the outer portion 1604 (e.g., seamlessly coupled). As shown in FIG. 10, each of the skin facing portion 1602 and the outer portion 1604 are substantially tubular. Furthermore, the skin facing portion 1602 and the outer portion 1604 are continuously formed such that no seams or stitches, seams, or adhesive are used to form the tubular textile-based electrode system 1600. The skin facing portion 1602 is configured to be folded about a fold line 1603 such that the skin facing portion 1602 overlaps the outer portion 1604 and is configured to contact the skin of the user during use. The system 1600 can include one or more stitches configured to couple the skin facing portion 1602 to the outer portion 1604, such that skin facing portion 1602 remains proximate to the outer portion 1604 during use. The electrodes 1610 can be continuously and seamlessly knitted into the skin facing portion 1602. The electrodes 1610 can be formed from a conductive material, for example, conductive yarn. The electrodes 1610 can be substantially similar to the electrode 110, 1110, 1210, 1310, or any other electrode described herein and are therefore, not described in further detail herein. The electrodes 1610 are configured to contact the skin of the user and sense an electrical signal corresponding to one or more physiological parameters of the user. In some embodiments, a padding member can be disposed on the skin facing portion 1602 behind the electrodes 1610. The padding member can be formed from any suitable material such as, for example, rubbery foam, a sponge, memory foam, a 3-D knitted porous fabric, any other suitable material or combination thereof. The padding member can be configured to urge the electrode towards the skin of the user. In some embodiments, the electrodes 1610 can be spaced equally around the circumference of the tubular skin facing portion 1602, for example, by at least about 10 cms, about 11 cms, 12 cms, 13 cms, 14 cms, 15 cms, 16 cms, 17 cms, 18 cms, 19 cms, or at least about 20 cms. This can allow design flexibility and enhance the quality of the measured electrical signals. While shown as including three electrodes 1610, any number of electrodes can be included in the skin facing portion 1602, for example, 2, 4, 5, 6 or even more.

The conductive pathways 1620 can be substantially similar to the conductive pathway 120, 1120, 1220, 1320, or any other conductive pathway described herein. The conductive pathways 1620 are seamlessly and continuously knitted to the electrodes 1610 using conductive yarn. The conductive pathways 1620 extend from the skin facing portion 1602 into the outer portion 1604 and are seamlessly and continuously knitted to the connector regions 1630. In this manner, the electrodes 1610 can be in electrical communication with the connector region 1630 via the conductive pathways 1620. The conductive pathways 1620 can be electrically insulated from the skin of the user and the outside environment by laminating or otherwise coating with an insulating material such as, for example, heat sealed adhesive, insulating membrane, polymers, plastic, mica, etc. In some embodiments, each of the conducting pathways 1620 can have a width of about 0.2 cm to about 2 cms, for example, about 0.4 cm, about 0.6 cm, about 0.8 cm, about 1 cm, about 1.2 cm about 1.4 cm, about 1.6 cm, or about 1.8 cm. In some embodiments, each of the conducting pathways 1620 can have a width of about 0.5 cm to about 1 cm.

The connector regions 1630 are disposed in the outer portion 1604. The connector regions 1630 are seamlessly and continuously knitted into the outer portion and coupled to the conductive pathways 1620 as described herein. While not shown, a connector, as described with respect to the system 100, 1100, 1200, 1300, or any other system described herein, can be coupled to each connector region 1630. The connectors can be configured to couple the connector regions 1630 to a connector assembly, for example, the connector assembly 160, or any other connector assembly described herein. The connector regions 1630 can be substantially similar to the connector regions 130, 1130, 1230, 1330, or any other connector region described herein, and therefore not described in further detail herein. While shown as including five connector regions 1630, any number of connecting regions can be included in the system 1600, for example, 2, 3, 4, 6, or even more. Furthermore, while shown as being arranged in a semi-circular array, the connecting regions 1630 can be included in any suitable configuration in the outer portion, for example, circular, elliptical, square, polygonal, triangular, asymmetric, etc.

In some embodiment, the connector regions 1630 can include openings configured to receive the connector. In such embodiments, the connectors can be electrically coupled to the conductive pathways 1620, for example, using mechanical coupling or a conductive adhesive.

Figure 11A:
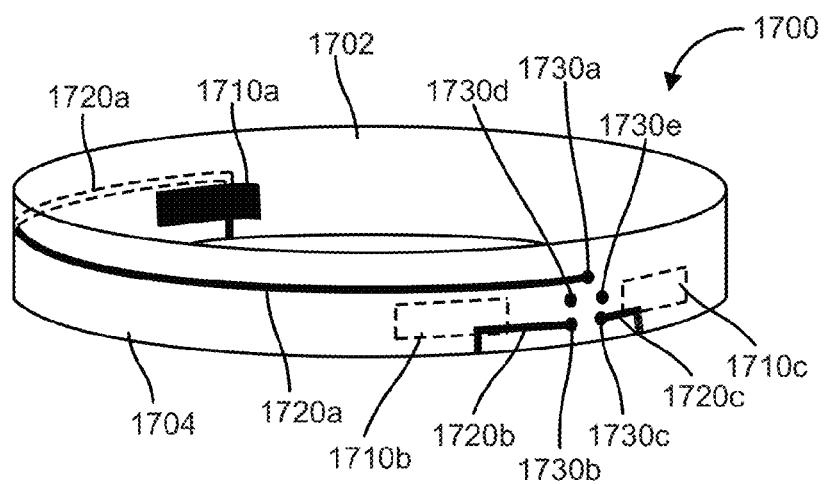
FIG. 11A shows a perspective view of a textile-based electrode system that includes a two layer band with the hidden components of the system shown in dashed lines, according to an embodiment.
Figure 11B:
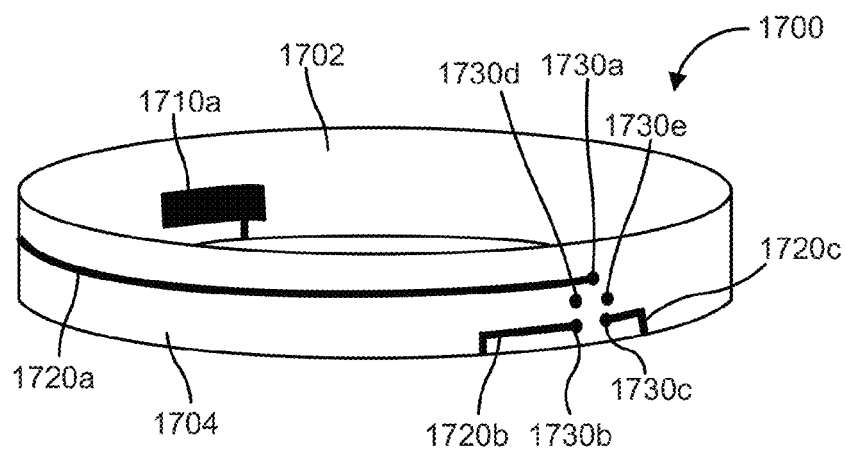
FIG. 11B shows a perspective view of the textile based electrode system of FIG. 11A.

In some embodiments, a textile-based electrode system can include a two layer band. Referring now to FIGS. 11A and 11B, a textile-based electrode system 1700 includes a skin facing portion 1702 and an outer portion 1704. The skin facing portion 1702 includes a first electrode 1710a, a second electrode 1710b, a third electrode 1710c (collectively referred to as "the electrodes 1710"), and at least a portion of a first conductive pathway 1720a, a second conductive pathway 1720b, and a third conductive pathway 1720c (collectively referred to as "the conductive pathways 1720"). The outer portion 1704 extends from the skin facing portion 1702 and includes a first connector region 1730a, a second connector region 1730b, a third connector region 1730c, a fourth connector region 1730d, a fifth connector region 1730e (collectively referred to as "the connector regions 1730"), and at least a portion of the conductive pathways 1720 which extend from the skin facing portion 1702 to the outer portion 1704. As shown in FIGS. 11A and 11B the system 1700 is substantially circular and can be included in any textile or garment, for example, a band, a shirt, a jersey, a vest, a bra, or any other wearable textile, such that the system 1700 can be used to measure one or more physiological parameters of a user.

The skin facing portion 1702 and the outer portion 1704 can be formed from a non-conductive material, for example, any of the materials described with respect to the first fabric layer included in the textile-based electrode system 100. Furthermore, the skin facing portion 1702 can be continuously formed with the outer portion 1704 (e.g., seamlessly coupled). The skin facing portion 1702 is folded over the outer portion 1704 such that the skin facing portion 1702 completely overlaps the outer portion 1704 and the system 1700 is a circular band. The system 1700 can include one or more stitches configured to couple the skin facing portion 1702 to the outer portion 1704, such that skin facing portion 1702 remains proximate to the outer portion 1704 during use.

The electrodes 1710 can be continuously and seamlessly knitted into the skin facing portion 1702. The electrodes 1710 can be formed from a conductive material, for example, conductive yarn. The electrodes 1710 can be substantially similar to the electrode 110, 1110, 1210, 1310, or any other electrode described herein and are therefore, not described in further detail herein. The electrodes 1710 are configured to contact the skin of the user and sense an electrical signal corresponding to one or more physiological parameters of the user during use. The electrodes 1710 can be disposed along the tubular skin facing portion 1702 with a predetermined spacing so as to capture biological signals from the user from different locations of the skins of the user. For example, in some embodiments, the electrodes 1710 can be disposed such that the electrodes are proximate to and/or aligned with the main organs of the user such as, for example, the heart and the lungs, during use. While shown as including three electrodes 1710, any number of electrodes can be included in the skin facing portion 1702, for example, 2, 4, 5, 6 or even more, as described with respect to the electrodes 1310 included in the system 1300. In some embodiments, the second electrode 1710b and the third electrode 1710c can be the sensing electrodes, and the first electrode 1710a can be a ground electrode. In some embodiments, a fourth electrode can be disposed in the skin facing portion 1702 proximal to the electrode 1710a. In some embodiments, the fourth electrode can be coupled to the first electrode 1710a and/or extend from the first electrode 1710a. In such embodiments, the fourth electrode can be configured to reduce background noise and thereby, improve signal quality. In some embodiments, a padding member can be disposed on the skin facing portion 1702 behind the electrodes 1710. The padding member can be formed from any suitable material such as, for example, rubbery foam, a sponge, memory foam, a 3-D knitted porous fabric (e.g., a 3-D knitted mesh or 3-D spacer knit), any other suitable material or combination thereof.

The conductive pathways 1720 can be substantially similar to the conductive pathway 120, 1120, 1220, 1320, or any other conductive pathway define herein. The conductive pathways 1720 are seamlessly and continuously knitted to the electrodes 1710, for example, using conductive yarn. The conductive pathways 1720 extend from the skin facing portion 1702 into the outer portion 1704 and are seamlessly and continuously knitted to the connector regions 1730. In this manner, the electrodes 1710 can be in electrical communication with the connector region 1730 via the conductive pathways 1720. The conductive pathways 1720 can be electrically insulated from the skin of the user and the outside environment by laminating or otherwise coating with an insulating material such as, for example, polymers, plastic, mica, etc.

The connector regions 1730 are disposed in the outer portion 1704. The connector regions 1730 are seamlessly and continuously knitted into the outer portion and coupled to the conductive pathways 1720 as described herein. While not shown, a connector, as described with respect to the system 100, 1100, 1200, 1300, or any other system described herein, can be coupled to each connector region 1730. The connectors can be configured to couple the connector regions 1730 to a connector assembly, for example, the connector assembly 160, or any other connector assembly described herein. The connector regions 1730 can be substantially similar to the connector regions 130, 1130, 1230, 1330, or any other connector region described herein, and therefore not described in further detail herein.

In some embodiment, the connector regions 1730 can include openings configured to receive the connector. In such embodiments, the connectors can be electrically coupled to the conductive pathways 1720, for example, using mechanical coupling or a conductive adhesive.

While shown as including seamlessly knitted electrodes, conductive pathways, and connector regions, any of the systems 1300, 1400, 1500, 1600, or 1700 can be formed similar to the systems 1100 and 1200 described herein. For example, in some embodiments, any of the systems 1300, 1400, 1500, 1600, or 1700 can include electrodes, conductive pathways, and/or connector regions that are disposed in separate portions, for example, a first fabric portion, a second fabric portion, and a third fabric portion respectively. In such embodiments, the electrodes and the conductive pathways can be electrically isolated from each other in an unfolded configuration in which the fabric portions are not folded. The electrodes, conductive pathways, and/or connector regions can be configured to be electrically coupled to each other in a folded configuration in which the fabric portions are folded. For example, in a partially folded configuration, the first fabric portion can be folded about a first fold axis or fold line and disposed adjacent to the second fabric portion such that the conductive pathways can be electrically coupled to the electrodes, for example, using conductive yarn. In the folded configuration, the second fabric portion can be folded about a second fold axis or fold line such that the first fabric portion is adjacent to the third fabric portion and disposed between the third fabric portion and the second fabric portion. Furthermore, the conductive pathways can be configured to be electrically coupled with the connector regions (e.g., connector regions that include conductive portions) or connectors disposed in opening defined by the connector regions.

Figure 12A:
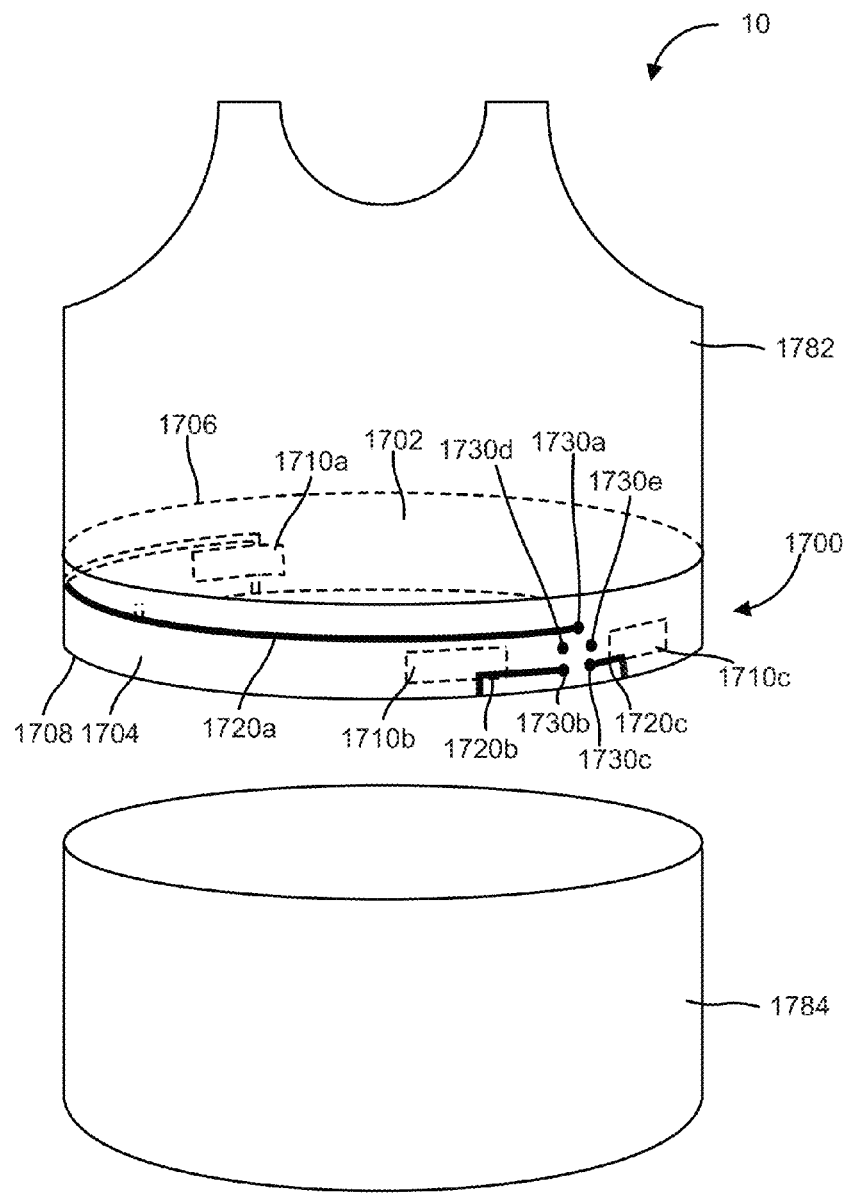
FIG. 12A shows a perspective view of a wearable garment that includes a textile based electrode system of FIG. 11A in a first configuration with the hidden components of the system shown in dashed lines, according to an embodiment.
Figure 12B:
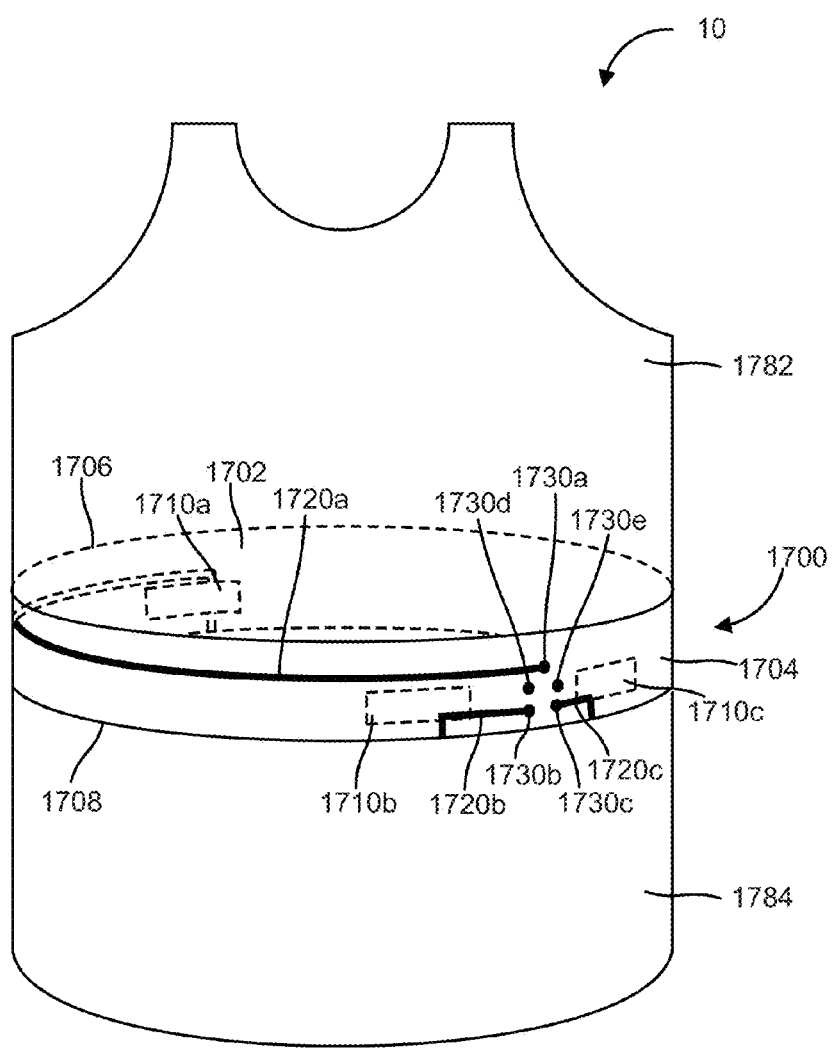
FIG. 12B shows a perspective view of the wearable garment of FIG. 12A in a second configuration.

In some embodiments, the system 1700 or any other system described herein can be included in a wearable garment. Referring now to FIGS. 12A and 12B, in some embodiments, a wearable garment 10 can include the textile-based electrode system 1700, a top fabric portion 1782 and a bottom fabric portion 1784. As shown in FIG. 12A, a top edge 1706 of the system 1700 can be coupled to the top fabric portion 1782 which is configured to contact the upper torso of a user during use. The top fabric portion 1782 and the bottom fabric portion 1784 can be formed from a non-conductive material and can be substantially similar to the material used to form the skin facing portion 1702 and the outer portion 1704 of the system 1700. A bottom fabric portion 1784 can also be coupled to a bottom edge 1708 of the system 1700. In some embodiments, the bottom fabric portion 1784 can be disposed over the outer portion 1704, for example, partially or completely overlapping the outer portion 1704. In such embodiments, the bottom fabric portion can be coupled to the top edge 1706 and/or the bottom edge 1708 of the system 1700. The bottom fabric portion 1784 can be substantially tubular and configured to contact a lower torso, for example, the midriff and or waist of the user during use. In some embodiments, the system 1700 can be knitted together with the top fabric portion 1782, and the bottom fabric portion 1784 can be coupled to the system 1700. In some embodiments, the bottom fabric portion 1784 can be knitted together with the system 1700 and the top fabric portion 1782 can be coupled to the system 1700.

The top fabric portion 1782 and/or the bottom fabric portion 1784 can be coupled to the system 1700 using any suitable means such as, for example, stitching, sewing, gluing, hot wire press, high frequency welding, ultrasonic welding, any other suitable coupling method or combination thereof. In this manner, the system 1700 or any other system described herein can be included in a wearable garment or textile. As shown herein, the wearable garment 10 can be a vest or a sports bra configured to measure one or more physiological parameters of the user as described herein. In some embodiments, the top fabric portion 1782 can include sleeves such that the wearable garment 10 can be a shirt, a t-shirt, or a jersey. In some embodiments, a cover layer, for example, a pocket, a sleeve, or a compartment can be included in the top fabric portion 1782 or the bottom fabric portion 1784. The cover layer can be configured to house, hide or otherwise conceal at least a portion of a connector assembly configured to be coupled to the connectors and thereby, to be in electrical communication with the electrodes 1710.

Figure 13:
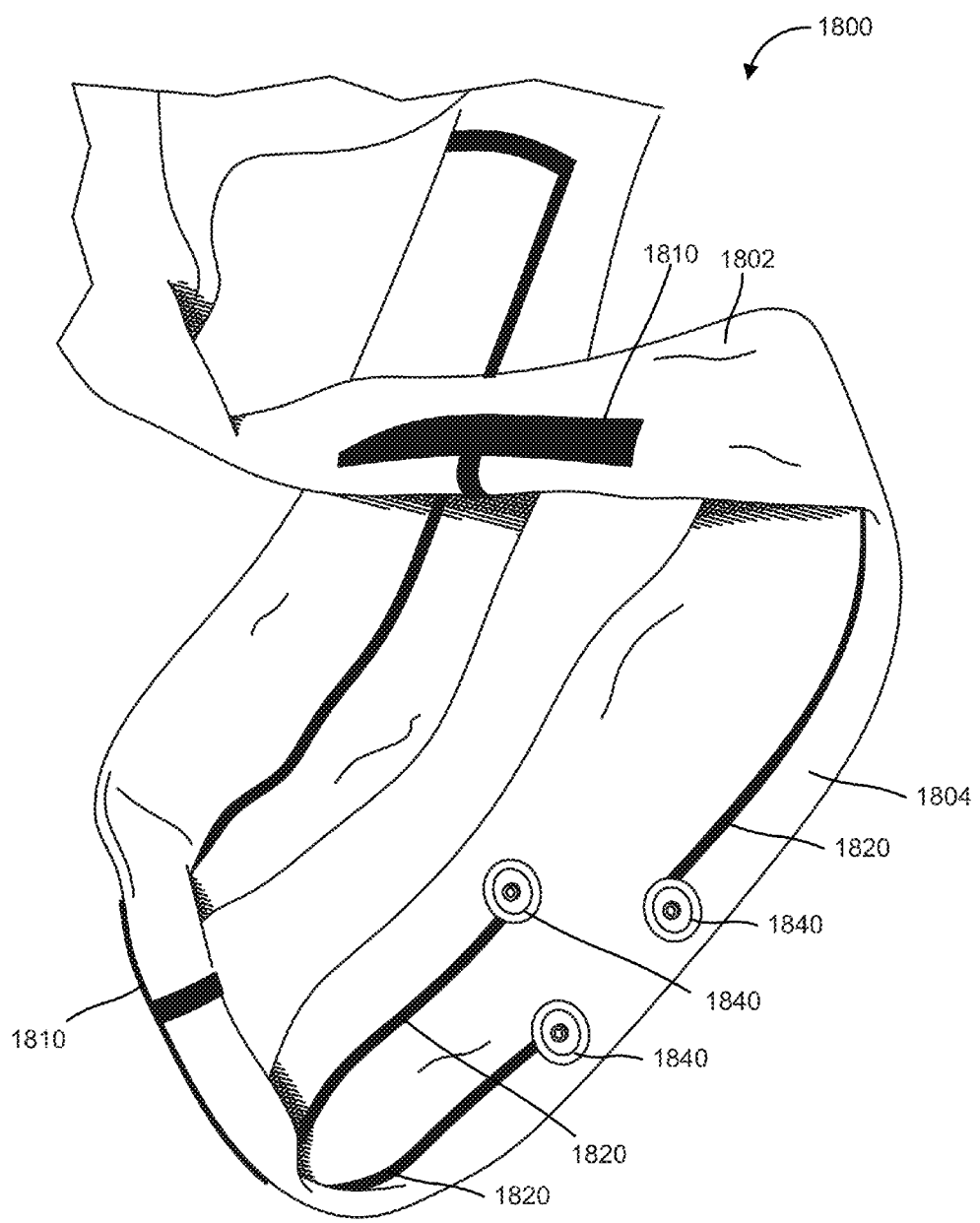
FIG. 13 shows a perspective view of a textile-based electrode system that includes a plurality of connectors, according to an embodiment.

As described herein, any of the textile-based electrode systems described herein, for example, the system 1100, 1200, 1300, 1700, or any other textile-based electrode system described herein can include connectors electrically coupled to the conductive pathways and/or connector regions included in the textile-based electrode systems. Referring now to FIG. 13, a textile based electrode system 1800 includes a skin facing portion 1802 and an outer portion 1804. The skin facing portion 1802 includes a plurality of electrodes 1810 and at least a portion of a plurality of conductive pathways 1820. The outer portion 1804 extends from the skin facing portion 1802 and includes a plurality of connectors 1840 coupled to the conductive pathways 1820 which extend from the skin facing portion 1802 into the outer portion 1804.

The skin facing portion 1802 and the outer portion 1804 can be formed from a non-conductive material, for example, any of the materials described with respect to the first fabric layer included in the textile-based electrode system 100. Furthermore, the skin facing portion 1802 can be continuously formed with the outer portion 1804 (e.g., seamlessly coupled). The skin facing portion 1802 is folded over the outer portion 1804 such that the skin facing portion 1802 completely overlaps the outer portion 1804 and the system 1800 can be a circular band. The system 1800 can include one or more stitches configured to couple the skin facing portion 1802 to the outer portion 1804, such that skin facing portion 1802 remains proximate to the outer portion 1804 during use.

The electrodes 1810 can be substantially similar to the electrodes 1710 or any other electrode described herein, and are therefore not described in further detail herein. The conductive pathways 1820 can be substantially similar to the conductive pathway 120, 1120, 1220, 1320, or any other conductive pathway define herein. The conductive pathways 1820 are seamlessly and continuously knitted to the electrodes 1810, for example, using conductive yarn. The conductive pathways 1820 extend from the skin facing portion 1802 into the outer portion 1804. The connectors 1840 can be disposed in the outer portion 1804, for example, in openings defined in the outer portion 1804 and can be configured to be electrically coupled to the conductive pathways 1820 (e.g., using mechanical coupling). In this manner, the electrodes 1810 can be in electrical communication with the connectors 1840 via the conductive pathways 1820. The conductive pathways 1820 can be electrically insulated from the skin of the user and the outside environment by laminating or otherwise coating with an insulating material such as, for example, heat sealed adhesive, insulating membrane, polymers, plastic, mica, etc.

As shown in FIG. 13, the connectors 1840 include male snap or press-fit button connector configured to be coupled to a female snap or press-fit button connector receivers included in a connector assembly (e.g., the connector assembly 160, or any other connector assembly described herein). In some embodiments, any other connector can be used, for example, pin-socket connector, a DIN connector, a banana connector, a hook connector, a magnetic connector, any other suitable connector or a combination thereof. The connectors 1840 can be configured to be removably coupled to the connector receivers with sufficient force such that the connector assembly remains coupled to the connectors 1840 during a user activity, for example, walking, jogging, running, dancing, sleeping, or any other activity. At the same time, the connectors 1840 can be configured to uncouple from the connector receivers with sufficient ease such that the user does not exert excessive force to uncouple the connector assembly from the connectors 1840 (e.g., to prevent excessive wear or tear of the outer portion 1804 of the system 1800).

Figure 14:
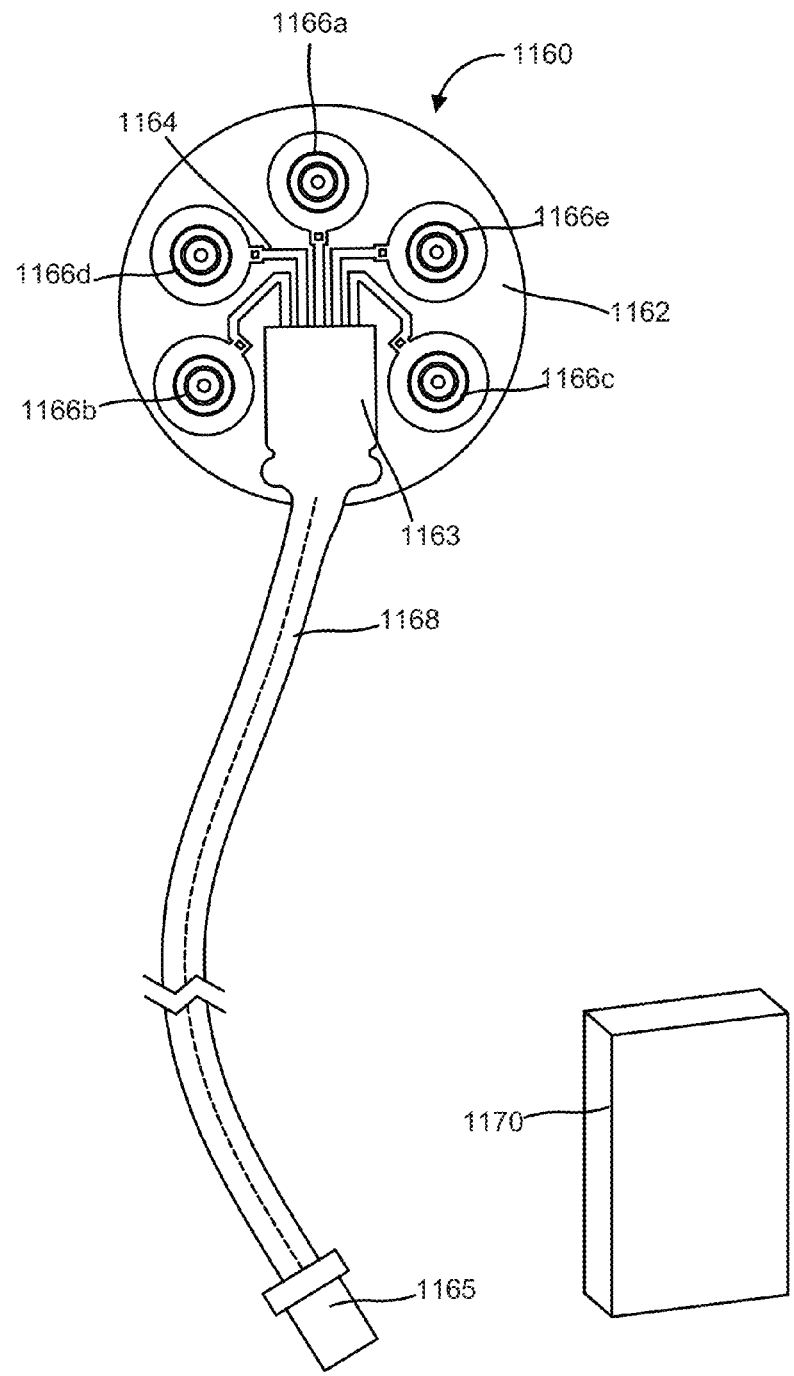
FIG. 14 shows a front view of a connector assembly and a processing module that can be coupled to the connector assembly, according to an embodiment.

As described herein, a connector assembly can include connector receivers configured to be coupled to connectors included in a system, for example, the system 100, 1100, 1200, 1300, 1400, 1500, 1600, 1700, 1800 or any other system described herein to a processing module. Referring now to FIG. 14, in some embodiments, a connector assembly 1160 can include a substrate 1162, an electrical circuit 1164, a first connector receiver 1166a, a second connector receiver 1166b, a third connector receiver 1166c, a fourth connector receiver 1166d, and a fifth connector receiver 1166e (collectively referred to as the "connector receivers 1166"), and an electric cable 1168. The connector assembly 1160 is configured to electrically couple to connectors included in a textile-based electrode system (e.g., the system 100, 1100, 1200, 1300, 1400, 1500, 1600, 1700, 1800 or any other system described herein) such that a plurality of electrodes included in the system can be in electric communication with a processing module 1170.

The substrate 1162 can be an insulating substrate that can provide a flat surface on which the electric circuit 1164 and the connector receivers 1166 are disposed. The substrate can be formed from any suitable electrically insulating and light weight material for example, plastics. The substrate can have an ergonomic shape such that the connector assembly 1160 can be disposed on the system (e.g., any of the systems described herein) without causing any discomfort to the user when the system is in use. While shown as being round, the substrate 1162 can have any suitable shape such as, for example, square, rectangular, triangular, elliptical, oval, polygonal, any other suitable shape or combination thereof.

The electrical circuit 1164 is disposed on the substrate 1162 and configured to couple the connector receivers 1166 to the electrical lead 1168. The electrical circuit 1164 can include a printed circuit that can include a plurality of electrodes. Each electrode of the plurality of electrodes can be configured to receive an electrical signal from a single connector receiver 1166.

The connector receivers 1166 include female snap-fit or press fit button connectors, configured to be removably coupled to male snap-fit or press fit button connectors (e.g., the connectors 1840). In some embodiments, the connector receivers 1166 can include any male or female connector receiver, for example, a pin socket connector, a DIN connector, a banana connector, a hook connector, a magnetic connector, any other suitable connector or combination thereof. As shown in FIG. 14, the connector assembly includes five connector receivers 1166 disposed in a semi-circular array. In some embodiments, the first connector receiver 1166a can be configured to receive an electrical signal from a first electrode included in a textile-based electrode system that is disposed on a front portion of a torso of a user (e.g., the chest proximate to the lungs). The second connector receiver 1166b can be configured to receive an electrical signal from a second electrode included in the system which is disposed near the bottom of the heart of the user (e.g., on the chest or the back), and the third connector receiver 1166c can be configured to receive an electrical signal from a third electrode disposed on the back of the user. Furthermore, the fourth connector receiver 1166d and the fifth connector receiver 1166e can be configured to receive electrical signals from a respiration sensor. In such embodiments, the respiration sensor can be included in the system (e.g., any of the systems described herein) or provided as a separate system.

In some embodiments, the connector assembly can include any number of connectors, for example, 2, 3, 4, 6, or even more, corresponding to the number of connectors included in a system which is configured to receive the connector assembly 1166. Furthermore, the connector receivers 1166 can be disposed in any suitable orientation or configuration corresponding to the orientation or configuration of the connectors included in the system (e.g., circular, elliptical, square, rectangular, triangular, asymmetric, etc.), such that the connector receivers 1166 can be coupled to the connector receivers only in a preferred orientation. In this manner, any incorrect or misaligned coupling of the connector receivers 1166 to the connectors can be prevented.

The electric cable 1168 includes a first end 1163 coupled to the electric circuit and a second end 1165 coupled to the processing module 1170. The electric cable 1168 can include a plurality of electrodes configured to receive an electrical signal from each of the connector receiver 1166 and communicate it to the processing module 1170.

The processing module 1170 can be configured to at least one of a filter, amplify, and/or measure an electrical signal. Furthermore, the processing module 1170 can be configured to communicate the signal data to an external device, for example, smart phone, a tablet, a computer, a remote server, a cloud server, or any other external device. The processing module 1170 can be substantially similar to the processing module 170. In some embodiments, the electronic components included in the processing module 1170 can be disposed in a sufficiently small and light weight housing such that the processing module 1170 can be disposed on a user (e.g., in a trouser, worn on an arm band, a thigh band, a wrist band, worn on a belt, disposed in a shirt pocket or a pocket of a system) without causing discomfort to the user or a restriction in movement during use. In some embodiments, the processing module 1170 can include a smart phone, or a mobile device.

Figure 15:
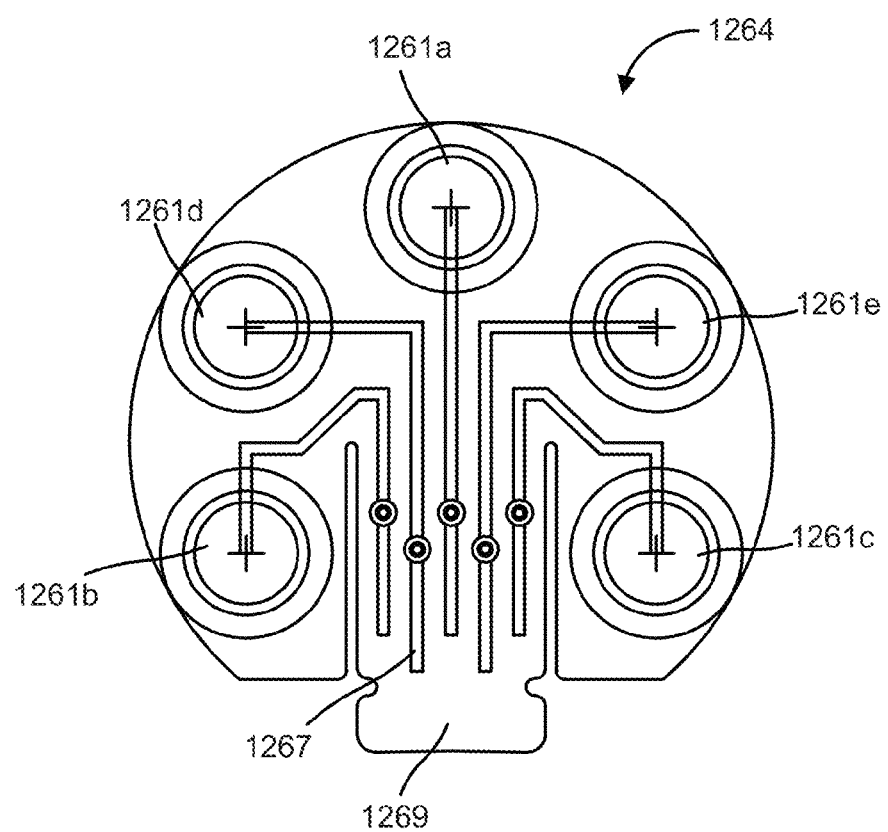
FIG. 15 shows an electrical circuit that can be included in a connector assembly, according to an embodiment.

FIG. 15 shows an electric circuit 1264 that can be included in a connector assembly, for example, the connector assembly 1160 or any other connector assembly described herein, according to an embodiment. The electric circuit 1264 includes a first connector receiver portion 1261a, a second connector receiver portion 1261b, a third connector receiver portion 1261c, a fourth connector receiver portion 1261d, and a fifth connector receiver portion 1261*e* (collectively referred to as "the connector receiver portions 1261"). A connector receiver, for example, the connector receiver 1166 or any other connector receiver described herein, can be fixedly disposed on each connector receiver portion 1261. Each connector receiver portion 1261 is served by an electrode 1267. The connector receiver disposed on the connector receiver portion 1261 can be coupled to the electrode 1267 by a solder, a weld, a conductive adhesive, a conductive epoxy, or any other suitable electrical coupling. The electrical circuit 1264 includes a coupling portion 1269 configured to be coupled to an electric cable, for example, the electrical cable 1168. While not shown, the electrical circuit 1264 can include electronic components such as, for example, resistors, capacitors, amplifiers, inductors, any other electronic components or combination thereof.

Figure 16A:
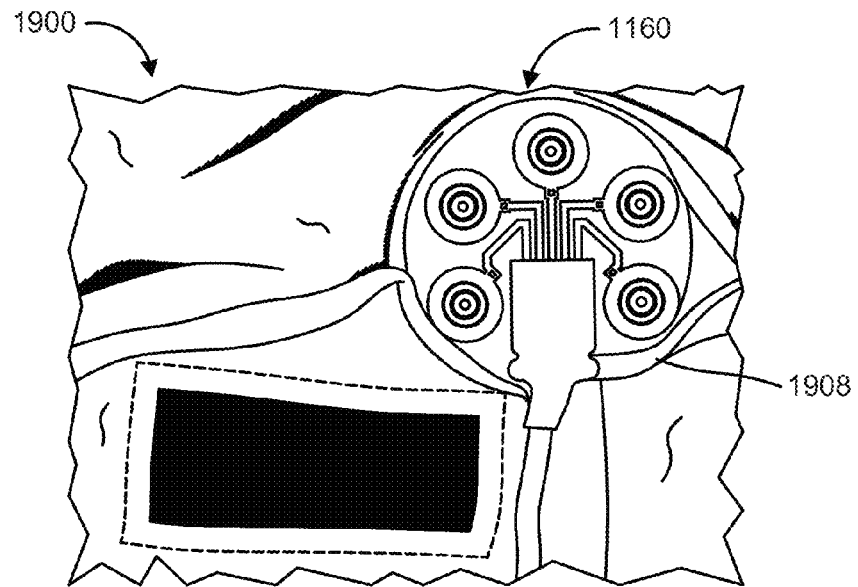
FIG. 16A shows a front view of a textile-based electrode system that includes a cover layer for housing a connector assembly in a first configuration, according to an embodiment.
Figure 16B:
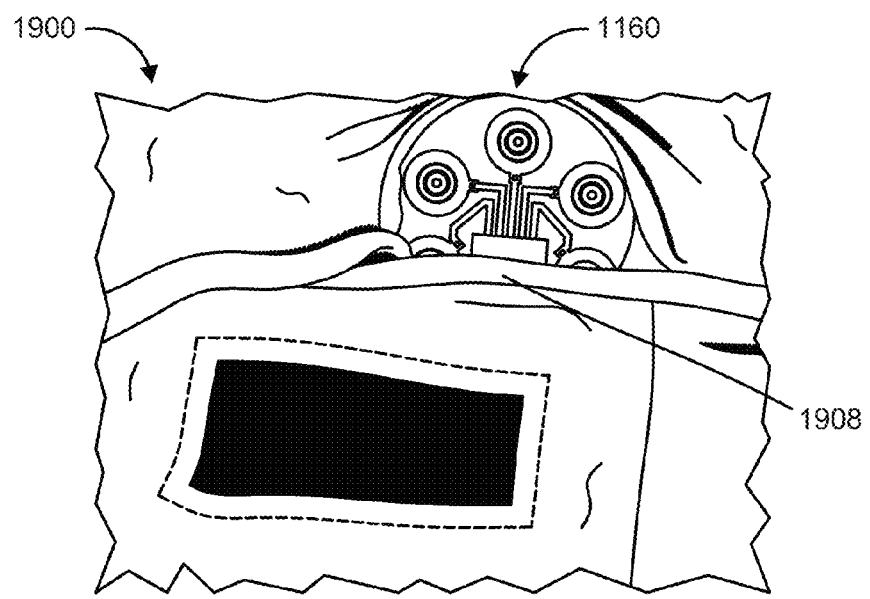
FIG. 16B shows the textile-based electrode system of FIG. 16A in a second configuration.

In some embodiments, a textile-based electrode system can include a cover layer for covering, hiding or otherwise concealing at least a portion of a connector assembly. Referring now to FIGS. 16A and 16B, a textile-based electrode system 1900 includes a cover layer 1908. The textile-based electrode system 1900 can be substantially similar to any of the systems described herein, for example, the system 100, 1100, 1200, 1300, 1400, 1500, 1600, 1700, 1800, or any other system described herein. As shown in FIG. 16A, the connector assembly 1160 (or any other connector assembly described herein) can be disposed on the system 1900, for example, coupled to connectors (e.g., the connectors 140, 1840, or any other connectors described herein) included in the system 1900. Once the connector assembly 1160 is disposed on the system 1900, the cover layer 1908 can be urged to move or slide over the connector assembly 1160 such that at least a portion of the connector assembly 1160 can be covered, hidden, or otherwise concealed by the cover layer 1908. In some embodiments, the cover layer 1908 can be a separate layer which can be pulled over the connector assembly 1160. In some embodiments, the cover layer 1908 can include a pocket or a compartment.

Figure 17:
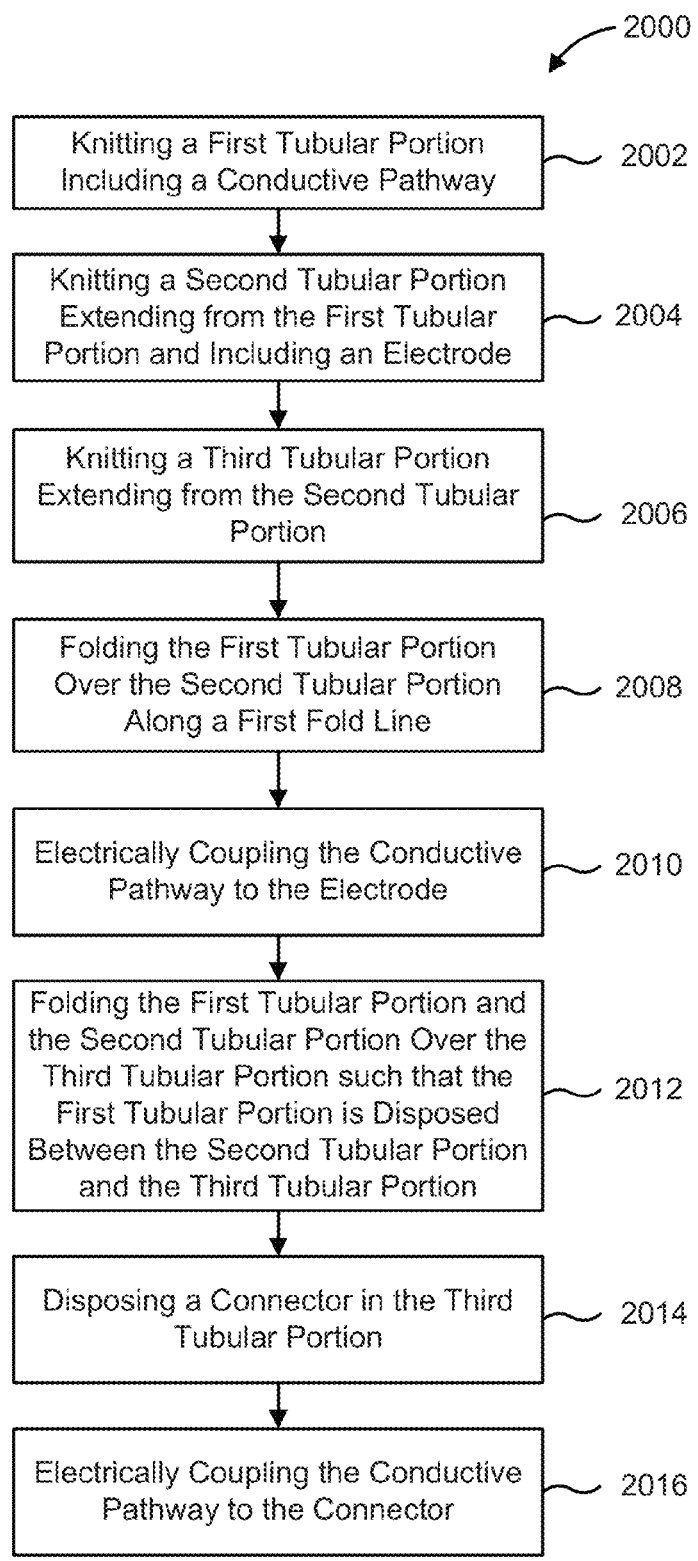
FIG. 17 is a schematic flow diagram showing a method of forming a textile-based electrode system, according to an embodiment.

FIG. 17 shows a schematic flow diagram of an exemplary method 2000 of forming a textile-based electrode system, for example, the system 100, 1100, 1200, 1300, 1400, 1500, 1600, 1700, 1800 or any other system described herein. The method 2000 includes knitting a first tubular portion including a conducting pathway 2002. The tubular portion can be knitted from a non-conductive material, for example, nylon, cotton, silk, ramie, polyester, latex, spandex, any other suitable non-conductive yarn or combination thereof. The conductive pathway can be continuously formed (e.g., seamlessly knit) with the first tubular portion. In some embodiments, the conductive pathway can be formed from conductive yarn. The conductive pathway can be substantially similar to the conductive pathway 120, 1120, 1220, 1320, or any other conductive pathway described herein. The method further includes knitting a second tubular portion extending from the first tubular portion and including an electrode 2004. The electrode can be continuously and seamlessly formed with the second tubular portion. In some embodiments, the electrode can be formed from conductive yarn. The electrode can be substantially similar to the electrode 110, 1110, 1210, 1310, or any other electrode described herein. A third tubular portion is knitted extending from the second tubular portion 2006. In some embodiments, the third tubular portion can include a hole, an aperture, or otherwise an opening configured to receive a connector. In some embodiments, the third tubular portion can include a connector region which can, for example, include conductive portions formed from conductive yarn. In such embodiments, the connector region can be continuously and seamlessly formed with the third tubular region, for example, using conductive yarn. The connector region can be configured to be electrically coupled to the conductive pathway, for example, using conductive yarn. In some embodiments, the first tubular portion, the second tubular portion, and the third tubular portion can be continuously formed (e.g., seamlessly knitted) with each other. The first tubular portion is folded over the second tubular portion along a first fold line 2008. The conductive pathway is then electrically coupled to the electrode 2010. In some embodiments, a first end of the conductive pathway is electrically coupled to the electrode. For example, the first end of the conductive pathway can be disposed adjacent to but not overlapping the electrode after folding the first tubular portion. In such embodiments, the conductive pathway can be electrically coupled to the electrode using, for example, conductive yarn. The first tubular portion and the second tubular portion are then folded over the third tubular portion such that the first tubular portion is disposed between the second tubular portion and the third tubular portion 2012. The connector is disposed in the third fabric portion 2014. The connector can include any suitable connector such as, for example, a male snap-fit or press-fit button connector, or any other connector described herein. The conductive pathway is then electrically coupled to the connector 2016. In some embodiments, a second end of the conductive pathway is electrically coupled to the connector. In such embodiments, the conductive pathway can be electrically coupled to the connector using any suitable means, for example, mechanical coupling, conductive adhesive or stitching with conductive yarn. In some embodiments, the first tubular portion is coupled to the second tubular portion after the first fold. Furthermore, the third tubular portion can be coupled to the second tubular portion and to the first tubular portion adjacent the first fold line such that the first tubular portion and the second tubular portion remains folded over the third tubular portion during use. The tubular portions can be coupled using any suitable means such as, for example, stitching, gluing, hot fusion bending, high frequency welding, ultrasonic welding, any other suitable coupling method or combination thereof.

In some embodiments, a padding member can be disposed adjacent the electrode between the first tubular portion and the second tubular portion. In some embodiments, the padding member can be disposed between the first tubular portion and the third tubular portion. The padding member can be configured to urge the electrode towards the skin of the user during user, for example, to maintain efficient contact between the electrode and the skin of the user and improve signal quality. In some embodiments, the padding member can be disposed between the first tubular portion and the second tubular portion before folding the first tubular portion about the first fold line. The padding member can be formed from any suitable material, as described herein.

In some embodiments, an insulating member can be disposed between the first tubular portion and the second tubular portion. The insulating member can be configured to electrically and/or mechanically isolate the conductive pathway from the second tubular portion. In some embodiments, the insulating member can be a first insulating member and a second insulating member can be disposed between the second tubular portion and the third tubular portion. The second insulating member can be configured to electrically and/or mechanically isolate the conductive pathway from the third tubular portion. In some embodiments, the first and second insulating members can be disposed before folding the first tubular portion over the second tubular portion along the first fold line. In some embodiments, the first insulating member can be disposed before folding the first tubular portion along the first fold line, and the second insulating member can be disposed after folding the first tubular portion along the first fold line. In some embodiments, the first and second insulating materials can include sheets or layers of an insulating material disposed between the first and second tubular portions, and the second and third tubular portions respectively. In some embodiments, the first and second insulating members can be disposed by laminating or overprinting a suitable insulating material (e.g., a heat sealed adhesive, insulating member, polymer, plastic, fabric, mica, etc.) over the conductive pathway.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A textile-based electrode system, comprising:
   a first fabric layer having an inner surface and an outer surface, the inner surface including a knitted electrode configured to be placed in contact with the skin of a user;
   a second fabric layer disposed and configured to contact the outer surface of the first fabric layer, the second fabric layer including a knitted conductive pathway configured to be electrically coupled to the knitted electrode;
   a third fabric layer disposed and configured to contact the second fabric layer, the third fabric layer including a knitted connector region configured to be electrically coupled to the knitted conductive pathway, a portion of the knitted connector region including an opening; and
   a connector disposed in the opening of the knitted connector region and configured to be electrically coupled to the knitted conductive pathway.

2. The system of claim 1, wherein the second fabric layer is folded about a first fold axis to place the second fabric layer in contact with the outer surface of the first fabric layer.

3. The system of claim 2, wherein the third fabric layer is folded about a second fold axis to place the third fabric layer in contact with the second fabric layer.

4. The system of claim 3, wherein first fabric layer is coupled to the second fabric layer and the third fabric layer along at least one of the first fold axis and the second fold axis such that the second fabric layer and the third fabric layer are maintained in the folded state.

5. The system of claim 1, wherein the knitted electrode and the knitted conductive pathway include conductive yarn.

6. The system of claim 1, wherein the first fabric layer is continuously formed with the second fabric layer.

7. The system of claim 6, wherein the first fabric layer is continuously formed with the third fabric layer.

8. The system of claim 1, wherein the knitted conductive pathway is electrically coupled to the knitted electrode using at least one of stitching, sewing, gluing, hot wire press, high frequency welding, and ultrasonic welding.

9. The system of claim 8, wherein the knitted conductive pathway is electrically coupled to the knitted electrode with conductive yarn.

10. The system of claim 1, wherein the connector is configured to electrically couple the knitted conductive pathway to a connector assembly.

11. The system of claim 10, wherein the connector is configured to be removably coupled to the connector assembly.

12. The system of claim 1, wherein the electrode is configured to measure at least one of a galvanic skin response (GSR), an electrocardiogram (ECG), a heart rate, a breathing rate, a breathing pattern, a rib cage perimeter, a rib cage volume, an electromyelogram, and a body temperature.

13. A textile-based electrode system, comprising:
   a first fabric portion including a knitted conductive pathway;
   a second fabric portion coupled to the first fabric portion and including a knitted electrode configured to be placed in contact with the skin of a user, the second fabric portion folded over the first fabric portion along a first fold line such that (a) the knitted electrode is configured to be electrically coupled to the knitted conductive pathway, and (b) the knitted electrode is configured to be adjacent to a first side of the knitted conductive pathway; and
   a third fabric portion coupled to the second fabric portion and including a connector region, the third fabric portion folded over the first fabric portion along a second fold line such that (a) the connector region is configured to be electrically coupled to the knitted conductive pathway, (b) the first fabric portion is disposed between the second fabric portion and the third fabric portion, and (c) the connector region is configured to be adjacent to a second side of the knitted conductive pathway,
   wherein the first side of the knitted conductive pathway is opposite to the second side of the knitted conductive pathway.

14. The system of claim 13, wherein the first fabric portion, the second fabric portion, and the third fabric portion are substantially tubular.

15. The system of claim 13, wherein the first fabric portion, the second fabric portion, and the third fabric portion are formed seamlessly.

16. The system of claim 13, wherein the knitted conductive pathway is coupled to at least one of the knitted electrode and the connector region using conductive yarn.

17. The system of claim 13, further comprising:
   a stitch configured to couple the second fabric portion to the first fabric portion such that the second fabric portion remains folded about the first fold line during use.

18. The system of claim 17, wherein the stitch is a first stitch, the system further comprising:
   a second stitch configured to couple the third fabric portion to the first fabric portion and the second fabric portion such that the third fabric portion remains folded about the second fold line during use.

19. The system of claim 13, wherein the connector region defines an opening through which a connector can be disposed.

20. The system of claim 13, wherein the connector region includes a conductive portion configured to be electrically coupled to the knitted conductive pathway.

* * * * *